US008563711B2

(12) United States Patent
Lee et al.

(10) Patent No.: US 8,563,711 B2
(45) Date of Patent: Oct. 22, 2013

(54) NUCLEIC ACID APTAMER CAPABLE OF BINDING SPECIFICALLY TO PANCREATIC CANCER CELLS OR TISSUES AND USE THEREOF

(75) Inventors: Dong Ki Lee, Seoul (KR); Dua Pooja, Gyeonggi-do (KR)

(73) Assignee: Sungkyunkwan University Foundation for Corporate Collaboration, Gyeonggi-do (KR)

( * ) Notice: Subject to any disclaimer, the term of this patent is extended or adjusted under 35 U.S.C. 154(b) by 0 days.

(21) Appl. No.: 13/375,347

(22) PCT Filed: Jun. 1, 2010

(86) PCT No.: PCT/KR2010/003536
§ 371 (c)(1),
(2), (4) Date: Feb. 22, 2012

(87) PCT Pub. No.: WO2010/140834
PCT Pub. Date: Dec. 9, 2010

(65) Prior Publication Data
US 2012/0142013 A1 Jun. 7, 2012

(30) Foreign Application Priority Data

Jun. 1, 2009 (KR) ........................ 10-2009-0047940

(51) Int. Cl.
*C07H 21/04* (2006.01)
*C12Q 1/68* (2006.01)
(52) U.S. Cl.
USPC ......................................... 536/24.5; 435/6.1
(58) Field of Classification Search
USPC ............................................. 536/24.5; 435/6
See application file for complete search history.

(56) References Cited

U.S. PATENT DOCUMENTS

| 2007/0160526 | A1 | 7/2007 | Bruce et al. |
| 2008/0188008 | A1 | 8/2008 | Sasaki et al. |
| 2008/0242742 | A1 | 10/2008 | Depinho et al. |

FOREIGN PATENT DOCUMENTS

WO 2007129114 A2 11/2007

OTHER PUBLICATIONS

Christian Moser, et al.; "The Direct Effects of Anti-Vascular Endothelial Growth Factor Therapy on Tumor Cells," Clinical Colorectal Cancer, 2007, pp. 564-571, vol. 6.

Christopher S. Gondi, et al. "Concepts in In Vivo siRNA Delivery for Cancer Therapy," Journal of Cellular Physiology, Apr. 23, 2009, pp. 285-291, vol. 220.
Jennifer F Lee, et al., "Aptamer therapeutics advance," Current Opinion in Chemical Biology, 2006, pp. 282-289, vol. 10.
James C. Gilbert, et al., "First-in-Human Evaluation of Anti-von Willebrand Factor Therapeutic Aptamer ARC1779 in Healthy Volunteers," Circulation, 2007, pp. 2678-2686, vol. 116.
Ke-Tai Guo, et al., "Cell-SELEX: Novel Perspectives of Aptamer-Based Therapeutics," International Journal of Molecular Sciences, 2008, pp. 668-678, vol. 9.
Dion A. Daniels, et al., "A tenascin-C aptamer identified by tumor cell SELEX: Systematic evolution of ligands by exponential enrichment," Proc. Natl. Acad. Sci. U.S.A, 2003, pp. 15416-15421, vol. 100.
Dihua Shangguan, et al., "Cell-Specific Aptamer Probes for Membrane Protein Elucidation in Cancer Cells," Journal of Proteome Research, 2008, pp. 2133-2139, vol. 7.
Hui William Chen, et al., "Molecular Recognition of Small-Cell Lung Cancer Cells Using Aptamers," Chem. Med. Chem., 2008, pp. 991-1001, vol. 3.
Randall Brand, MD, et al., "Risk Factors for Pancreatic Adenocarcinoma: Are We Ready for Screening and Surveillance?" Curr. Gastroenterol. Rep., 2005, pp. 122-127, vol. 7.
Michael Xiang Lee, et al., "Screening for Early Pancreatic Ductal Adenocarcinoma: An Urgent Call!" Journal of the Pancreas, 2009, pp. 104-108, vol. 10.
Nabeel Bardeesy, et al., "Pancreatic Cancer Biology and Genetics," Nature Rev. Cancer, 2002, pp. 897-909, vol. 2.
Alexandros Koliopanos, et al., "Molecular aspects of carcinogenesis in pancreatic cancer," Hepatobiliary Pancreat Dis Int., 2008, pp. 345-356, vol. 7.
Jiehua Zhou et al., "Aptamer-targeted cell-specific RNA interference," Silence, A journal of RNA regulation, 2010, pp. 1-10.
Ted C. Chu, et al., "Aptamer: Toxin Conjugates that Specifically Target Prostate Tumor Cells," Cancer Res., 2006, pp. 5989-5992, vol. 66.
Huaizhi Kang, et al., "A Liposome-based Nanostructure for Aptamer Directed Delivery," Chem Comm. (Camb.), 2010. pp. 249-251, vol. 46.

*Primary Examiner* — J E Angell
(74) *Attorney, Agent, or Firm* — Tristan A. Fuierer; Andrew D. Gerschutz; Moore & Van Allen, PLLC

(57) ABSTRACT

The present invention relates to a nucleic acid aptamer which can specifically recognize and bind to pancreatic cancer cells or tissues. The nucleic acid aptamer can bind specifically only to pancreatic cancer cells or tissues without binding to normal pancreatic cancer tissue, and thus can be effectively used as a composition for diagnosing and treating pancreatic cancer. In addition, the nucleic acid aptamer can detect not only the terminal pancreatic cancer cell line Capan-1, but also the early pancreatic cancer cell line Panc-1, and thus can be used for early diagnosis of pancreatic cancer, thereby contributing to increasing the survival rate of pancreatic cancer patients.

22 Claims, 20 Drawing Sheets

FIG. 2

| | Sequence | No of repeats |
|---|---|---|
| Consensus SQ1 | ATACCAGCTTATTCAATT GCCTGATTAG CGGTATCACG ATTACTTACC TTCGTTGCTG -AGATAGTAAGTGCAATCT (SEQ ID No: 20) | (16 clones) |
| Consensus SQ2 | ATACCAGCTTATTCAATT GCCTGAAAAG CTATCGCCCA ATTCGCAGTG ATATCCTTTA -AGATAGTAAGTGCAATCT (SEQ ID No: 21) | (4 clones) |
| Consensus SQ3 | ATACCAGCTTATTCAATT GCCTGAAAAC CTGGTCTCTC TGTCAGCAAA AGATAGTAA -GTGCAATCT (SEQ ID No: 22) | (4 clones) |
| Consensus SQ4 | ATACCAGCTTATTCAATT GCCTGAGTAG CTGGGTCCGT CCCCACACAT TACCATTTGT -AGATAGTAAGTGCAATCT (SEQ ID No: 23) | (4 clones) |
| SQ5 | ATACCAGCTTATTCAATT GCCTGAAAAC TGGTGTACCT CTTTGCCCTA TCTTATCTGG -AGATAGTAAGTGCAATCT (SEQ ID No: 24) | (3 clones) |
| SQ6 | ATACCAGCTTATTCAATT GCCTGAAGAC TGGATATACT CTTAAGCATT TCTATAATCG -AGATAGTAAGTGCAATCT (SEQ ID No: 25) | (2 clones) |
| SQ7 | ATACCAGCTTATTCAATT GCCTGAAACT GCTGCATCGT CTCCCACGTA TTACACATGA -AGATAGTAAGTGCAATCT (SEQ ID No: 26) | (2 clones) |
| SQ8 | ATACCAGCTTATTCAATT GCCTGAAAAG TTGAACTCCA AATACGCGCT G AGATAGTA -AGTGCAATCT (SEQ ID No: 27) | (2 clones) |
| S49 | ATACCAGCTTATTCAATT GCCTGAAAAG TGGCCTCCCT ACAAAGAACT TATATCATCC -AGATAGTAAGTGCAATCT (SEQ ID No: 28) | |
| S20 | ATACCAGCTTATTCAATT GCCTGAAAAG TTTATCCCCC TTTTAGCGTT TACCATAATG -AGATAGTAAGTGCAATCT (SEQ ID No: 29) | |
| S59 | ATACCAGCTTATTCAATT ACCTGAAAAC TGGTTTCCGG CATCCCGTAT TGCGGCTTTA C -AGATAGTAAGTGCAATCT (SEQ ID No: 30) | |
| S11 | ATACCAGCTTATTCAATT GCCTGAAGAG CGAAGTAAAT CTCTCACTGC GTCACTACA -AGATAGTAAGTGCAATCT (SEQ ID No: 31) | |
| S52 | ATACCAGCTTATTCAATT ACCTGAGTAG CGTTTCCCGG CATTATACTA TAAACTT AGATA -GTAAGTGCAATCT (SEQ ID No: 32) | |
| S68 | ATACCAGCTTATTCAATT CCTGAAAGTT TGGATATCTT GGCGCTTGAC TAGAAAACTT G -AAATTTGT AGATAGTAAGTGCAATCT (SEQ ID No: 33) | |
| S3 | ATACCAGCTTATTCAATT CTTATGTTCA TGCCAGCGCA ATTGCC AGATAGTAAGTGCA -ATCT (SEQ ID No: 34) | |

FIG. 13
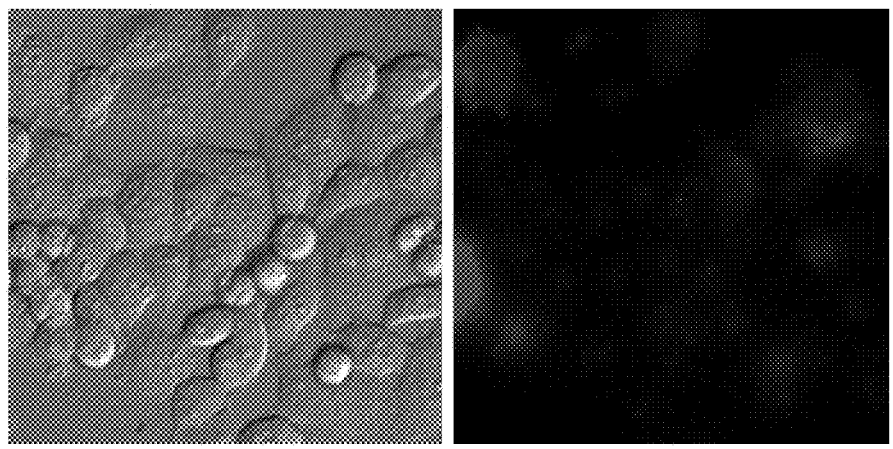
SQ 2
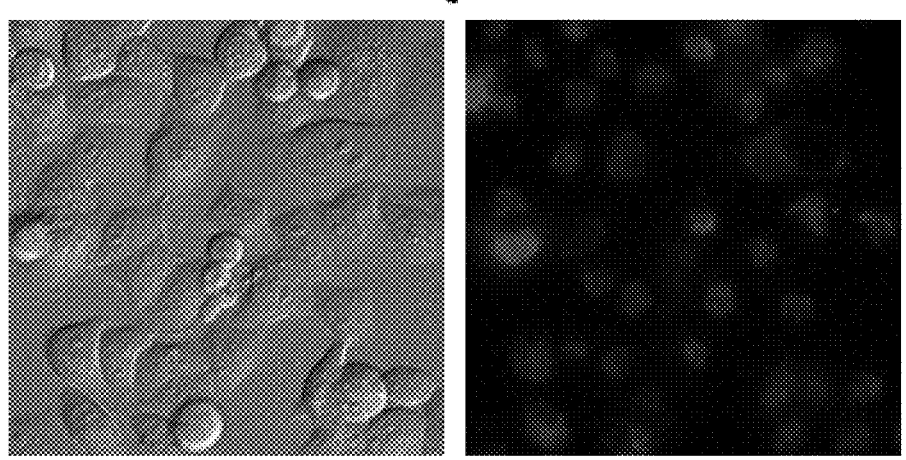
SQ 4
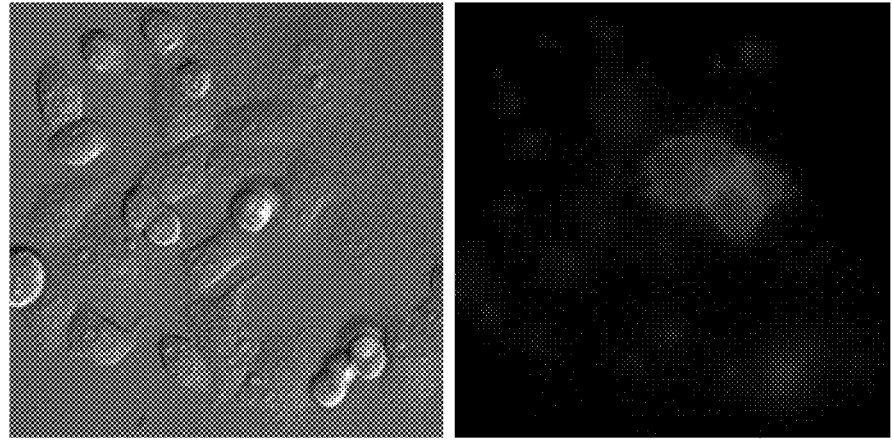
SQ 8

FIG. 16
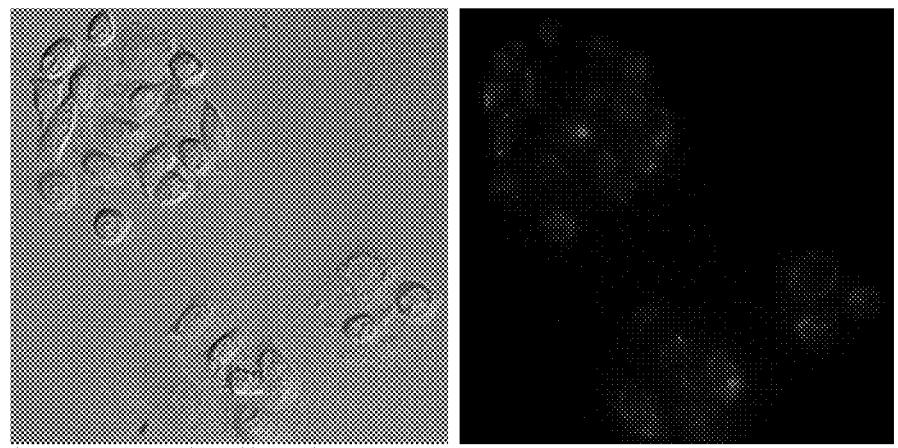
(a) SQ 2
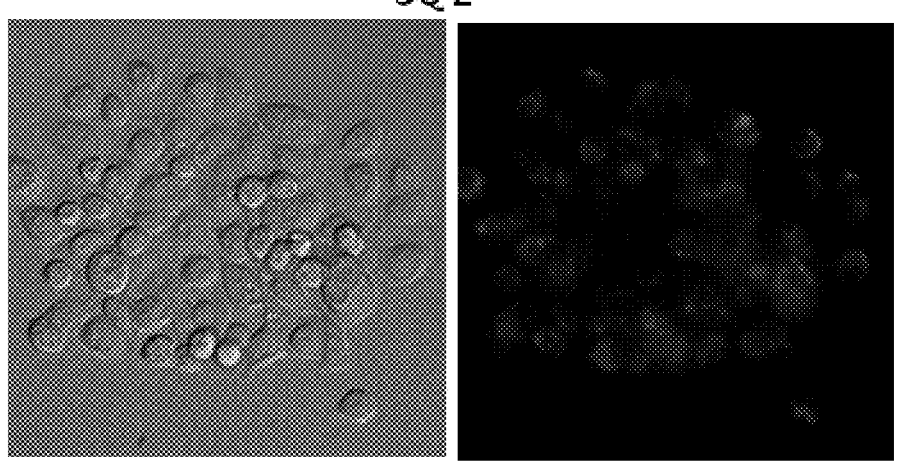
(b) SQ 4
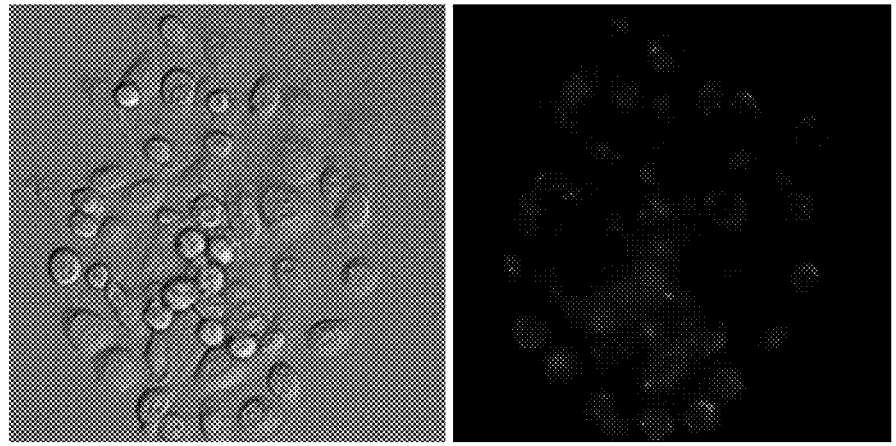
(c) SQ 8

Capan-1: SQ2 > SQ8 > SQ1 > SQ4 > SQ7 ≈ SQ6 ≈ SQ5 ≈ SQ3

SEQUENCE LISTING

<160> NUMBER OF SEQ ID NOS: 41

<210> SEQ ID NO 1
<211> LENGTH: 76
<212> TYPE: RNA
<213> ORGANISM: Artificial Sequence
<220> FEATURE:
<223> OTHER INFORMATION: Synthetic Construct

<400> SEQUENCE: 1
auaccagcuu auucaauugc cugauuagcg guaucacgau uacuuaccuu cguugcugag        60
auaguaagug caaucu                                                       76

<210> SEQ ID NO 2
<211> LENGTH: 76
<212> TYPE: RNA
<213> ORGANISM: Artificial Sequence
<220> FEATURE:
<223> OTHER INFORMATION: Synthetic Construct

<400> SEQUENCE: 2
auaccagcuu auucaauugc cugaaaagcu aucgcccaau ucgcagugau auccuuuaag        60
auaguaagug caaucu                                                       76

<210> SEQ ID NO 3
<211> LENGTH: 66
<212> TYPE: RNA
<213> ORGANISM: Artificial Sequence
<220> FEATURE:
<223> OTHER INFORMATION: Synthetic Construct

<400> SEQUENCE: 3
auaccagcuu auucaauugc cugaaaaccu ggucucucug ucagcaaaag auaguaagug        60
caaucu                                                                  66

<210> SEQ ID NO 4
<211> LENGTH: 76
<212> TYPE: RNA
<213> ORGANISM: Artificial Sequence
<220> FEATURE:
<223> OTHER INFORMATION: Synthetic Construct

<400> SEQUENCE: 4
auaccagcuu auucaauugc cugaguagcu ggguccgucc ccacacauua ccauuguag        60 auaguaagug caaucu                                                       76

<210> SEQ ID NO 5
<211> LENGTH: 76
<212> TYPE: RNA
<213> ORGANISM: Artificial Sequence
<220> FEATURE:
<223> OTHER INFORMATION: Synthetic Construct

<400> SEQUENCE: 5
auaccagcuu auucaauugc cugaaaacug guguaccucu uugcccuauc uuaucuggag        60
auaguaagug caaucu                                                       76

<210> SEQ ID NO 6
<211> LENGTH: 76
<212> TYPE: RNA
<213> ORGANISM: Artificial Sequence
<220> FEATURE:

<223> OTHER INFORMATION: Synthetic Construct

<400> SEQUENCE: 6
auaccagcuu auucaauugc cugaagacug gauauacucu uaagcauuuc uauaaucgag    60
auaguaagug caaucu    76

<210> SEQ ID NO 7
<211> LENGTH: 76
<212> TYPE: RNA
<213> ORGANISM: Artificial Sequence
<220> FEATURE:
<223> OTHER INFORMATION: Synthetic Construct

<400> SEQUENCE: 7
auaccagcuu auucaauugc cugaaacugc ugcaucgucu cccacguauu acacaugaag    60
auaguaagug caaucu    76

<210> SEQ ID NO 8
<211> LENGTH: 67
<212> TYPE: RNA
<213> ORGANISM: Artificial Sequence
<220> FEATURE:
<223> OTHER INFORMATION: Synthetic Construct

<400> SEQUENCE: 8
auaccagcuu auucaauugc cugaaaaguu gaacuccaaa uacgcgcuga gauaguaagu    60
gcaaucu    67

<210> SEQ ID NO 9
<211> LENGTH: 76
<212> TYPE: RNA
<213> ORGANISM: Artificial Sequence
<220> FEATURE:
<223> OTHER INFORMATION: Synthetic Construct

<400> SEQUENCE: 9
auaccagcuu auucaauugc cugaaaagug gccucccuac aaagaacuua uaucauccag    60
auaguaagug caaucu    76

<210> SEQ ID NO 10
<211> LENGTH: 76
<212> TYPE: RNA
<213> ORGANISM: Artificial Sequence
<220> FEATURE:
<223> OTHER INFORMATION: Synthetic Construct

<400> SEQUENCE: 10
auaccagcuu auucaauugc cugaaaaguu uauccccuu uuagcguuua ccauaaugag    60
auaguaagug caaucu    76

<210> SEQ ID NO 11
<211> LENGTH: 77
<212> TYPE: RNA
<213> ORGANISM: Artificial Sequence
<220> FEATURE:
<223> OTHER INFORMATION: Synthetic Construct

<400> SEQUENCE: 11
auaccagcuu auucaauuac cugaaaacug guuuccggca ucccguauug cggcuuuaca    60
gauaguaagu gcaaucu    77

<210> SEQ ID NO 12

-continued

```
<211> LENGTH: 75
<212> TYPE: RNA
<213> ORGANISM: Artificial Sequence
<220> FEATURE:
<223> OTHER INFORMATION: Synthetic Construct

<400> SEQUENCE: 12
auaccagcuu auucaauugc cugaagagcg aaguaaaucu cucacugcgu cacuacaaga      60
uaguaagugc aaucu                                                      75

<210> SEQ ID NO 13
<211> LENGTH: 73
<212> TYPE: RNA
<213> ORGANISM: Artificial Sequence
<220> FEATURE:
<223> OTHER INFORMATION: Synthetic Construct

<400> SEQUENCE: 13
auaccagcuu auucaauuac cugaguagcg uuucccggca uuauacuaua aacuuagaua      60
guaagugcaa ucu                                                        73

<210> SEQ ID NO 14
<211> LENGTH: 85
<212> TYPE: RNA
<213> ORGANISM: Artificial Sequence
<220> FEATURE:
<223> OTHER INFORMATION: Synthetic Construct

<400> SEQUENCE: 14
auaccagcuu auucaauucc ugaaaguuug gauaucuugg cgcuugacua gaaaacuuga      60
aauuuguaga uaguaagugc aaucu                                           85

<210> SEQ ID NO 15
<211> LENGTH: 62
<212> TYPE: RNA
<213> ORGANISM: Artificial Sequence
<220> FEATURE:
<223> OTHER INFORMATION: Synthetic Construct

<400> SEQUENCE: 15
auaccagcuu auucaauucu uauguucaug ccagcgcaau ugccagauag uaagugcaau      60
cu                                                                    62

<210> SEQ ID NO 16
<211> LENGTH: 76
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (19)..(58)
<223> OTHER INFORMATION: n is a, c, g, or t

<400> SEQUENCE: 16
ataccagctt attcaattnn nnnnnnnnn nnnnnnnnnn nnnnnnnnnn nnnnnnnnag      60
atagtaagtg caatct                                                     76

<210> SEQ ID NO 17
<211> LENGTH: 42
<212> TYPE: DNA
<213> ORGANISM: Artificial Sequence
<220> FEATURE:
<223> OTHER INFORMATION: Synthetic Construct
```

-continued

```
<400> SEQUENCE: 17
ggtaatacga ctcactatag ggagatacca gcttattcaa tt                              42

<210> SEQ ID NO 18
<211> LENGTH: 18
<212> TYPE: DNA
<213> ORGANISM: Artificial Sequence
<220> FEATURE:
<223> OTHER INFORMATION: Synthetic Construct

<400> SEQUENCE: 18
agattgcact tactatct                                                        18

<210> SEQ ID NO 19
<211> LENGTH: 18
<212> TYPE: DNA
<213> ORGANISM: Artificial Sequence
<220> FEATURE:
<223> OTHER INFORMATION: Synthetic Construct

<400> SEQUENCE: 19
agattgcact tactatct                                                        18

<210> SEQ ID NO 20
<211> LENGTH: 76
<212> TYPE: DNA
<213> ORGANISM: Artificial Sequence
<220> FEATURE:
<223> OTHER INFORMATION: Synthetic Construct

<400> SEQUENCE: 20
ataccagctt attcaattgc ctgattagcg gtatcacgat tacttacctt cgttgctgag          60
atagtaagtg caatct                                                          76

<210> SEQ ID NO 21
<211> LENGTH: 76
<212> TYPE: DNA
<213> ORGANISM: Artificial Sequence
<220> FEATURE:
<223> OTHER INFORMATION: Synthetic Construct

<400> SEQUENCE: 21
ataccagctt attcaattgc ctgaaaagct atcgcccaat tcgcagtgat atcctttaag          60
atagtaagtg caatct                                                          76

<210> SEQ ID NO 22
<211> LENGTH: 66
<212> TYPE: DNA
<213> ORGANISM: Artificial Sequence
<220> FEATURE:
<223> OTHER INFORMATION: Synthetic Construct

<400> SEQUENCE: 22
ataccagctt attcaattgc ctgaaaacct ggtctctctg tcagcaaaag atagtaagtg          60
caatct                                                                     66

<210> SEQ ID NO 23
<211> LENGTH: 76
<212> TYPE: DNA
<213> ORGANISM: Artificial Sequence
<220> FEATURE:
<223> OTHER INFORMATION: Synthetic Construct

<400> SEQUENCE: 23
```

```
ataccagctt attcaattgc ctgagtagct gggtccgtcc ccacacatta ccatttgtag    60
atagtaagtg caatct                                                    76

<210> SEQ ID NO 24
<211> LENGTH: 76
<212> TYPE: DNA
<213> ORGANISM: Artificial Sequence
<220> FEATURE:
<223> OTHER INFORMATION: Synthetic Construct

<400> SEQUENCE: 24
ataccagctt attcaattgc ctgaaaactg gtgtacctct ttgccctatc ttatctggag    60
atagtaagtg caatct                                                    76

<210> SEQ ID NO 25
<211> LENGTH: 76
<212> TYPE: DNA
<213> ORGANISM: Artificial Sequence
<220> FEATURE:
<223> OTHER INFORMATION: Synthetic Construct

<400> SEQUENCE: 25
ataccagctt attcaattgc ctgaagactg gatatactct taagcatttc tataatcgag    60
atagtaagtg caatct                                                    76

<210> SEQ ID NO 26
<211> LENGTH: 76
<212> TYPE: DNA
<213> ORGANISM: Artificial Sequence
<220> FEATURE:
<223> OTHER INFORMATION: Synthetic Construct

<400> SEQUENCE: 26
ataccagctt attcaattgc ctgaaactgc tgcatcgtct cccacgtatt acacatgaag    60
atagtaagtg caatct                                                    76

<210> SEQ ID NO 27
<211> LENGTH: 67
<212> TYPE: DNA
<213> ORGANISM: Artificial Sequence
<220> FEATURE:
<223> OTHER INFORMATION: Synthetic Construct

<400> SEQUENCE: 27
ataccagctt attcaattgc ctgaaaagtt gaactccaaa tacgcgctga gatagtaagt    60
gcaatct                                                              67

<210> SEQ ID NO 28
<211> LENGTH: 76
<212> TYPE: DNA
<213> ORGANISM: Artificial Sequence
<220> FEATURE:
<223> OTHER INFORMATION: Synthetic Construct

<400> SEQUENCE: 28
ataccagctt attcaattgc ctgaaaagtg gcctccctac aaagaactta tatcatccag    60
atagtaagtg caatct                                                    76

<210> SEQ ID NO 29
<211> LENGTH: 76
<212> TYPE: DNA
<213> ORGANISM: Artificial Sequence
<220> FEATURE:
```

<223> OTHER INFORMATION: Synthetic Construct

<400> SEQUENCE: 29
ataccagctt attcaattgc ctgaaaagtt tatccccctt ttagcgttta ccataatgag    60
atagtaagtg caatct    76

<210> SEQ ID NO 30
<211> LENGTH: 77
<212> TYPE: DNA
<213> ORGANISM: Artificial Sequence
<220> FEATURE:
<223> OTHER INFORMATION: Synthetic Construct

<400> SEQUENCE: 30
ataccagctt attcaattac ctgaaaactg gtttccggca tcccgtattg cggctttaca    60
gatagtaagt gcaatct    77

<210> SEQ ID NO 31
<211> LENGTH: 75
<212> TYPE: DNA
<213> ORGANISM: Artificial Sequence
<220> FEATURE:
<223> OTHER INFORMATION: Synthetic Construct

<400> SEQUENCE: 31
ataccagctt attcaattgc ctgaagagcg aagtaaatct ctcactgcgt cactacaaga    60
tagtaagtgc aatct    75

<210> SEQ ID NO 32
<211> LENGTH: 73
<212> TYPE: DNA
<213> ORGANISM: Artificial Sequence
<220> FEATURE:
<223> OTHER INFORMATION: Synthetic Construct

<400> SEQUENCE: 32
ataccagctt attcaattac ctgagtagcg tttcccggca ttatactata aacttagata    60
gtaagtgcaa tct    73

<210> SEQ ID NO 33
<211> LENGTH: 85
<212> TYPE: DNA
<213> ORGANISM: Artificial Sequence
<220> FEATURE:
<223> OTHER INFORMATION: Synthetic Construct

<400> SEQUENCE: 33
ataccagctt attcaattcc tgaaagtttg gatatcttgg cgcttgacta gaaaacttga    60
aatttgtaga tagtaagtgc aatct    85

<210> SEQ ID NO 34
<211> LENGTH: 62
<212> TYPE: DNA
<213> ORGANISM: Artificial Sequence
<220> FEATURE:
<223> OTHER INFORMATION: Synthetic Construct

<400> SEQUENCE: 34
ataccagctt attcaattct tatgttcatg ccagcgcaat tgccagatag taagtgcaat    60
ct    62

<210> SEQ ID NO 35

```
<211> LENGTH: 25
<212> TYPE: RNA
<213> ORGANISM: Artificial Sequence
<220> FEATURE:
<223> OTHER INFORMATION: Synthetic Construct

<400> SEQUENCE: 35
agcuuauuca auurccugar dmbbb                                            25

<210> SEQ ID NO 36
<211> LENGTH: 58
<212> TYPE: RNA
<213> ORGANISM: Artificial Sequence
<220> FEATURE:
<223> OTHER INFORMATION: Synthetic Construct

<400> SEQUENCE: 36
auaccagcuu auucaauugc cugaaaagcu aucgcccaau ucgcagugau auccuuua        58

<210> SEQ ID NO 37
<211> LENGTH: 58
<212> TYPE: RNA
<213> ORGANISM: Artificial Sequence
<220> FEATURE:
<223> OTHER INFORMATION: Synthetic Construct

<400> SEQUENCE: 37
gccugaaaag cuaucgccca auucgcagug auauccuuua agauaguaag ugcaaucu       58

<210> SEQ ID NO 38
<211> LENGTH: 53
<212> TYPE: RNA
<213> ORGANISM: Artificial Sequence
<220> FEATURE:
<223> OTHER INFORMATION: Synthetic Construct

<400> SEQUENCE: 38
agcuuauuca auugccugaa aagcuaucgc ccaauucgca gugauauccu uua            53

<210> SEQ ID NO 39
<211> LENGTH: 45
<212> TYPE: RNA
<213> ORGANISM: Artificial Sequence
<220> FEATURE:
<223> OTHER INFORMATION: Synthetic Construct

<400> SEQUENCE: 39
agcuuauuca auugccugaa aagcuaucgc ccaauucgca gugau                     45

<210> SEQ ID NO 40
<211> LENGTH: 50
<212> TYPE: RNA
<213> ORGANISM: Artificial Sequence
<220> FEATURE:
<223> OTHER INFORMATION: Synthetic Construct

<400> SEQUENCE: 40
auaccagcuu auucaauugc cugaaaagcu aucgcccaau ucgcagugau                50

<210> SEQ ID NO 41
<211> LENGTH: 25
<212> TYPE: RNA
<213> ORGANISM: Artificial Sequence
```

-continued

```
<220> FEATURE:
<223> OTHER INFORMATION: Synthetic Construct

<400> SEQUENCE: 41
agcuuauuca auugccugaa aagcu                                              25
```

NUCLEIC ACID APTAMER CAPABLE OF BINDING SPECIFICALLY TO PANCREATIC CANCER CELLS OR TISSUES AND USE THEREOF

CROSS-REFERENCE TO RELATED APPLICATIONS

This application is filed under the provisions of 35 U.S.C. §371 and claims the priority of International Patent Application No. PCT/KR2010/003536 filed on 1 Jun. 2010 entitled "Nucleic Acid Aptamer Capable of Binding Specifically to Pancreatic Cancer Cells or Tissues and Use Thereof" in the name of Dong Ki LEE, et al., which claims priority of Korean Patent Application No. 10-2009-0047940 filed on 1 Jun. 2009, both of which are hereby incorporated by reference herein in their entirety.

TECHNICAL FIELD

The present invention relates to a nucleic acid aptamer which can specifically recognize and bind to pancreatic cancer cells or tissues and can thus be used to diagnose and treat pancreatic cancer, and to the use thereof.

BACKGROUND ART

In recent years, studies on a number of biomarkers for cancer diagnosis and treatment have been conducted. Among them, cancer cell-specific membrane proteins are considered as the most appropriate biomarkers as they are often shed in the body fluids in detectable amounts and clinical presentation in body fluids is always preferred over invasive methods of biopsy sampling. Besides, membrane proteins are also attractive because of their potential use in cancer imaging and targeted therapeutic strategies.

Meanwhile, the field of biomarker identification primarily relies on 2D gel electrophoresis (2D-GE) mass spectroscopy. However elucidation of membrane proteins using this technique has a significant limitation. Only 30% of the total cellular proteins are from membrane and of this only 5% can be detected using 2D-GE. Therefore as an alternative, specific probes has been developed for membrane proteins that can be used as tools to identify the bound target.

In the last decade, there has been a renaissance in the field of nucleic acid probes-aptamers; that can bind to the target protein with high affinity and specificity. Particularly, aptamers which are isolated using the technique SELEX (Systemic Enrichment of Ligands using Exponential Enrichment) have been developed for a number of disease-associated proteins, and many of them are currently in clinical trials as therapeutic moieties teemselves or as tools for imaging or drug delivery (Lee, J. F. et al., *Curr Opin Chem. Biol.*, 10(3): 282, 2006; Gilbert, J. C. et al., *Circulation.*, 116(23): 2678, 2007).

Aptamers can be selected against complex targets, that is, live cells and tissues, using the cell-SELEX technique in addition to the prior SELEX technique (Guo et al. *Int. J. Mol. Sci.*, 9(4): 668, 2008). The cell-SELEX technique has an advantage in that it allows the development of aptamers for diseased cells even when surface marker targets are unknown. In addition, the cell-SELEX technique is more advantageous than the prior SELEX process, because target proteins cannot show their original properties in their isolated state, and thus target proteins which are in a physiological state allow a more functional approach during a selection process. Thus, an ssDNA aptamer for tenascin-C was first developed using the cell-SELEX approach (Daniels et al., *Proc. Natl. Acad. Sci. U.S.A.*, 100(26):15416, 2003), and then a PTK7 (protein tyrosine kinase) aptamer for acute myeloid cells (Shangguan, D. et al., *J. Proteome. Res.*, 7(5): 2133, 2008) and a DNA aptamer for small cell lung cancer cells (Chen H. W. et al., *Chem. Med. Chem.*, 3(6): 991, 2008) were also developed. Using substractive SELEX DNA aptamers have been synthesized that can bind to differentiated PC12 cells but not parental cells thus are useful in clinical diagnosis (Brand, R. & Mahr, C., *Curr. Gastroenterol. Rep.*, 7(2):122, 2005; Lee, M. X. & Saif, M. W., *Jop.*, 10(2): 104, 2009). However, the Cell-SELEX technique requires limited control by an optimized and specific selection process because of the complexity of cell surface proteasomes. Thus, a proper negative selection process is essential for the success of the Cell-SELEX process.

Meanwhile, pancreatic adenocarcinoma is the $14^{th}$ common cancer worldwide and the $4^{th}$ leading cause of cancer related deaths in US alone. Around 90% of these pancreatic tumors are ductal adenocarcinomas (PDAC)s (Bardeesy, N. & DePinho, R. A., *Nat. Rev. Cancer*, 2(12):897, 2002). It is a highly aggressive malignancy with a very low median survival rate. The high rate of mortality associated with is attributable to poor prognosis and profound resistance to conventional chemotherapeutic measures (Koliopanos, A. et al., *Hepatobiliary Pancreat. Dis. Int.*, 7(4):345, 2008). Only 15-20% of such tumors are resectable and limitation of early diagnostic markers pose a major problem in its timely detection (Brand, R. & Mahr, C., *Curr. Gastroenterol. Rep.*, 7(2): 122, 2005; Lee, M. X. & Saif, M. W., *Jop.*, 10(2):104, 2009). Thus, there has been a need for the development of a novel pancreatic biomarker which can promote early diagnosis and assist in the development of effective therapeutic agents.

Accordingly, the present inventors have made extensive efforts to isolate a pancreatic cancer-specific cancer which can be used for the early diagnosis and treatment of pancreatic cancer. As a result, the present inventors have selected an aptamer, which specifically binds only to a pancreatic cancer cell line, by the cell-SELEX (Systematic Evolution of Ligands by EXponential enrichment) process, and have found that the selected aptamer binds specifically only to a pancreatic cancer cell line without binding to normal pancreatic tissue, thereby completing the present invention.

DISCLOSURE OF INVENTION

It is an object of the present invention to provide a nucleic acid aptamer binding specifically to pancreatic cancer cells or tissues.

Another object of the present invention is to provide a method of detecting pancreatic cancer using said nucleic acid aptamer.

Still another object of the present invention is to provide a composition for diagnosing or treating pancreatic cancer, which contains said nucleic acid aptamer.

To achieve the above objects, the present invention provides a nucleic acid aptamer of 20-100 nts, which comprises any one nucleic acid sequence selected from the group consisting of nucleic acid sequences set forth in SEQ ID NO: 14, SEQ ID NO: 15 and SEQ ID NO: 35, or a fragment thereof, and is capable of binding specifically to pancreatic cancer cells or tissues, wherein U in the nucleic acid sequence is T if the nucleic acid aptamer is DNA.

The present invention also provides a method of detecting pancreatic cancer using said nucleic acid aptamer or a nucleic acid aptamer comprising a chemical modification thereof.

The present invention also provides a composition for diagnosing or treating pancreatic cancer, which contains said nucleic acid aptamer or a nucleic acid aptamer comprising a chemical modification thereof.

The present invention also provides a method of diagnosing or treating pancreatic cancer, which comprises administering said nucleic acid aptamer or a nucleic acid aptamer comprising a chemical modification thereof.

The present invention also provides the use of said nucleic acid aptamer or a nucleic acid aptamer comprising a chemical modification thereof, for diagnosis or treatment of pancreatic cancer.

The present invention provides a sensor for diagnosing pancreatic cancer, having said nucleic acid aptamer binding specifically to pancreatic cells or tissues immobilized thereon.

The present invention also provides a kit for diagnosing pancreatic cancer, which contains said nucleic acid aptamer or a nucleic acid aptamer comprising a chemical modification thereof.

The present invention also provides a method of detecting pancreatic cancer using said sensor or kit for diagnosing pancreatic cancer.

The present invention also provides a pancreatic cancer-specific drug delivery composition containing said nucleic acid aptamer or a nucleic acid aptamer comprising a chemical modification thereof.

The present invention also provides a method of detecting a pancreatic cancer cell-specific surface biomarker using said nucleic acid aptamer or a nucleic acid aptamer comprising a chemical modification thereof.

Other features and embodiments of the present invention will be more apparent from the following detailed descriptions and the appended claims

BRIEF DESCRIPTION OF THE DRAWINGS

FIG. 2 shows the results of sequencing of an aptamer pool selected in the 14$^{th}$ round of the cell-SELEX process according to the schematic view shown in FIG. 1.

FIG. 13 is a set of photographs showing the results of observing the binding affinities of aptamers SQ2, SQ4 and SQ8 of the present invention for the pancreatic cancer cell line Pan-1 by fluorescence detection.

FIG. 16 is a set of photographs showing the results of observing the binding affinities of aptamers SQ2, SQ4 and SQ8 of the present invention for pancreatic cancer cell line Hapaf-II by fluorescence detection.

BEST MODE FOR CARRYING OUT THE INVENTION

Figure 1:
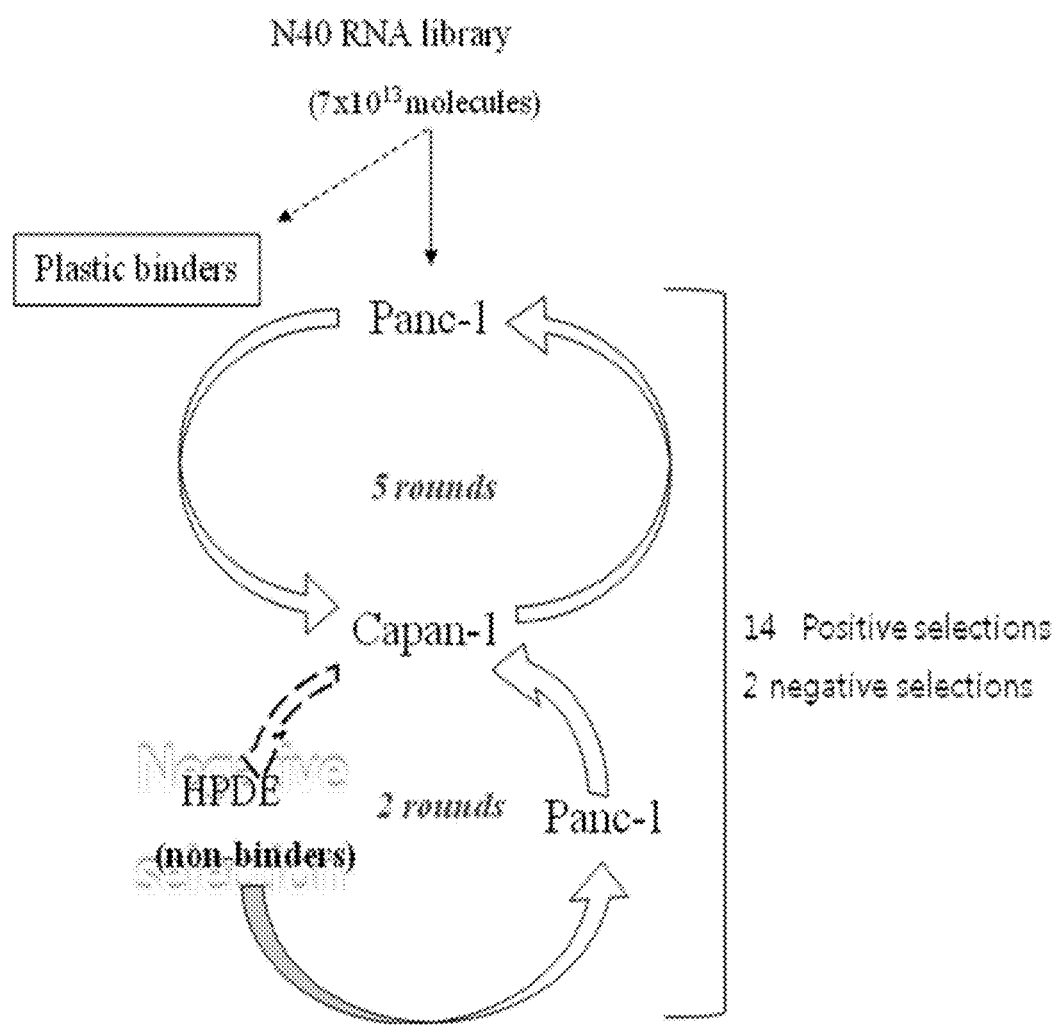
FIG. 1 is a schematic view showing a process of selecting aptamers binding specifically to pancreatic cancer cells or tissues according to the present invention.

Unless defined otherwise, all technical and scientific terms used herein have the same meaning as commonly understood by one of ordinary skill in the art to which the invention pertains. Generally, the nomenclature used herein and the experiment methods are those well known and commonly employed in the art.

The definition of main terms used in the detailed description of the invention is as follows.

As used herein, the term "nucleic acid aptamer" refers to a small single-stranded oligonucleotide that can recognize specifically to its target with high affinity.

As used herein, the term "sample" refers to a composition that might contain a marker for a pancreatic cancer to be analyzed. Examples of the sample include pancreatic tissues, pancreatic cells, blood, serum, plasma, saliva, phlegm, and urine.

As used herein, the phrase "nucleic acid sequence having a homology of at least 90%, but less than 100%" refers to a nucleic acid sequence which comprises an addition, deletion or substitution of one to several nucleotides relative to a reference sequence to have a sequence homology of at least 90%, but less than 100%, with the reference sequence, and to show a pancreatic cancer cell-binding affinity similar to the reference sequence.

In one aspect, the present invention is directed to a nucleic acid aptamer which comprises any one nucleic acid sequence selected from the group consisting of a nucleic acid sequence of AGCUUAUUCAAUURCCUGARDMBBB (R=G or A; D=A, U or G; M=A or C; and B=G, C or U; SEQ ID NO: 35) and nucleic acid sequences set forth in the following SEQ ID NO: 14 and SEQ ID NO: 15, or a fragment thereof, and is capable of binding specifically to pancreatic cancer cells or tissues.

In the present invention, the nucleic acid sequence set forth in SEQ ID NO: 35 is preferably AGCUUAUUCAAUUGC-CUGAAAAGCU (SEQ ID NO: 41), and the nucleic acid aptamer, which comprises the nucleic acid sequence set forth in SEQ ID NO: 35 and can bind specifically to pancreatic cancer cells or tissues, may comprise any one nucleic acid sequence selected from nucleic acid sequences set forth in the following SEQ ID NO: 1 through SEQ ID NO: 13.

```
SQ1:
                                       (SEQ ID NO: 1)
5'-AUACCAGCUUAUUCAAUU GCCUGAUUAG CGGUAUCACG

AUUACUUACC UUCGUUGCUG AGAUAGUAAGUGCAAUCU-3'

SQ2:
                                       (SEQ ID NO: 2)
5'-AUACCAGCUUAUUCAAUU GCCUGAAAAG CUAUCGCCCA

AUUCGCAGUG AUAUCCUUUA AGAUAGUAAGUGCAAUCU-3'

SQ3:
                                       (SEQ ID NO: 3)
5'-AUACCAGCUUAUUCAAUU GCCUGAAAAC CUGGUCUCUC

UGUCAGCAAA AGAUAGUAAGUGCAAUCU-3'

SQ4:
                                       (SEQ ID NO: 4)
5'-AUACCAGCUUAUUCAAUU GCCUGAGUAG CUGGGUCCGU

CCCCACACAU UACCAUUUGU AGAUAGUAAGUGCAAUCU-3'

SQ5:
                                       (SEQ ID NO: 5)
5'-AUACCAGCUUAUUCAAUU GCCUGAAAAC UGGUGUACCU

CUUUGCCCUA UCUUAUCUGG AGAUAGUAAGUGCAAUCU-3'

SQ6:
                                       (SEQ ID NO: 6)
5'-AUACCAGCUUAUUCAAUU GCCUGAAGAC UGGAUAUACU

CUUAAGCAUU UCUAUAAUCG AGAUAGUAAGUGCAAUCU-3'
```

```
SQ7:
                                       (SEQ ID NO: 7)
5'-AUACCAGCUUAUUCAAUU GCCUGAAACU GCUGCAUCGU

CUCCCACGUA UUACACAUGA AGAUAGUAAGUGCAAUCU-3'

SQ8:
                                       (SEQ ID NO: 8)
5'-AUACCAGCUUAUUCAAUU GCCUGAAAAG UUGAACUCCA

AAUACGCGCU G AGAUAGUAAGUGCAAUCU-3'

S49:
                                       (SEQ ID NO: 9)
5'-AUACCAGCUUAUUCAAUU GCCUGAAAAG UGGCCUCCCU

ACAAAGAACU UAUAUCAUCC AGAUAGUAAGUGCAAUCU-3'

S20:
                                       (SEQ ID NO: 10)
5'-AUACCAGCUUAUUCAAUU GCCUGAAAAG UUUAUCCCCC

UUUUAGCGUU UACCAUAAUG AGAUAGUAAGUGCAAUCU-3'

S59:
                                       (SEQ ID NO: 11)
5'-AUACCAGCUUAUUCAAUU ACCUGAAAAC UGGUUUCCGG

CAUCCCGUAU UGCGGCUUUA C AGAUAGUAAGUGCAAUCU-3'

S11:
                                       (SEQ ID NO: 12)
5'-AUACCAGCUUAUUCAAUU GCCUGAAGAG CGAAGUAAAU

CUCUCACUGC GUCACUACA AGAUAGUAAGUGCAAUCU-3'

S52:
                                       (SEQ ID NO: 13)
5'-AUACCAGCUUAUUCAAUU ACCUGAGUAG CGUUUCCCGG

CAUUAUACUA UAAACUU AGAUAGUAAGUGCAAUCU-3'

S68:
                                       (SEQ ID NO: 14)
5'-AUACCAGCUUAUUCAAUU CCUGAAAGUU UGGAUAUCUU

GGCGCUUGAC UAGAAAACUU GAAAUUUGU AGAUAGUAAGU

GCAAUCU-3'

S3:
                                       (SEQ ID NO: 15)
5'-AUACCAGCUUAUUCAAUU CUUAUGUUCA UGCCAGCGCA

AUUGCC AGAUAGUAAGUGCAAUCU-3'
```

The underlined portions of the 5'-terminus and 3'-terminus of each of the above aptamers are portions introduced for PCR amplification and cDNA synthesis as can be seen in following SEQ ID NO: 16.

Herein, the total number of nucleotides in the aptamer may be 20-200 nts, and preferably 20-100 nts. Preferably, the total number of nucleotides in the aptamer may be 25 nts or more or 85 nts or less. If the total number of nucleotides in the aptamer is small, the chemical synthesis and large-amount production of the aptamer will be easier and advantages in terms of costs will be obtained. Also, the aptamer will be easily chemically modified, will be highly stable in vivo and will have low toxicity. In addition, each nucleotide contained in the aptamer may comprise one or more chemical modification which is the same or different, and for example, may be a nucleotide substituted by any atom or group at the 2' position of ribose. As examples of any such atom or group, a nucleotide substituted by a hydrogen atom, a fluorine atom or an —O-alkyl group (e.g., —O-Me group), an —O-acyl group (e.g., —O—CHO group), or an amino group (e.g., —NH$_2$ group) can be mentioned. Furthermore, the nucleic acid aptamer is provided in the form of a single-stranded DNA or RNA molecule. In the present invention, if the nucleic acid is DNA, "U" in the nucleic acid sequence is to be read as "T", and it will be obvious to a person of ordinary skill in the art that this sequence falls within the scope of the present invention.

In one Example of the present invention, as shown in FIG. 1, the aptamers having the nucleic acid sequences set forth in SEQ ID NOS: 1 to 15 were selected through the SELEX process, and then the affinities of the selected aptamers were measured using a real-time PCR assay, a fluorescence detection method and an equilibrium filtration method. As a result, it was found that the nucleic acid sequences set forth in SEQ ID NOS: 1 to 15 did bind specifically to a pancreatic cancer cell line.

The nucleic acid aptamers according to the present invention are shown to have commonly conserved regions, such as CCUGA, GCCUGAAA, or AGCUUAUUCAAUURC-CUGARDMBBB (SEQ ID NO: 35). The presence of such commonly conserved regions means that a nucleic acid sequence having a homology of at least 90%, but less than 100%, with any one selected from among the nucleic acid sequences set forth in SEQ ID NO: 1 to SEQ ID NO: 15, is a nucleic acid aptamer that can bind specifically to a pancreatic cancer cell line. Regarding the similarity of sequence between the nucleic acid aptamers according to the present invention, if any nucleic acid comprises an addition, deletion or substitution of one to several nucleotides relative to any one nucleic acid sequence selected among the nucleic acid sequences of SEQ ID NOS: 1 to 15 to have a sequence homology of at least 90%, but less than 100%, it will show a pancreatic cancer cell line-binding affinity similar to the nucleic acid aptamers according to the present invention. Particularly, in one Example of the present invention, it was found that, even when portions of the 5' terminal and 3' terminal regions of the aptamer according to the present invention were deleted, the aptamer showed affinity for a pancreatic cancer cell line. Such test results demonstrate that, if any nucleic acid sequence comprises an addition, deletion or substitution of one to several nucleotides relative to any one nucleic acid sequence selected among the nucleic acid sequences of the present invention to have a sequence homology of at least 90%, but less than 100%, it will show a pancreatic cancer cell line-binding affinity similar to the nucleic acid aptamers according to the present invention.

Meanwhile, in another Example of the present invention, it was found that a 14$^{th}$ aptamer pool including the nucleic acid sequences of SEQ ID NOS: 1 to 15 did not substantially bind human cancer cell lines other than a pancreatic cancer cell line, suggesting that the aptamer pool specifically detect the pancreatic cancer cell line. Particularly, the affinities of the isolated aptamers SQ1, SQ2 and SQ6 for pancreatic cancer cell lines were observed using a fluorescence detection method in comparison with a normal human pancreatic ductal cell line (HPEDE). As a result, it was found that the aptamers specifically detected both the pancreatic cancer cell lines Capan-1 and Panc-1 indicating that the terminal stage and initial state of pancreatic cancer, respectively, suggesting that the aptamers according to the present invention can detect pancreatic cancer markers and thus can be advantageously used for diagnosis of pancreatic cancer. Particularly, ability of detecting Pacn-1 of the aptamers according to the present invention suggests that the aptamers allows the early diagnosis of pancreatic cancer. In another Example of the present invention, it was shown that the nucleic acid aptamers according to the present invention did bind specifically not only the pancreatic cancer cell line used in the positive selection process, but also other pancreatic cancer cell lines, suggesting that the aptamers can be advantageously used for substantial diagnosis of pancreatic cancer. In addition, in another Example of the present invention, it was found that the nucleic acid aptamers according to the present invention did not recognize cancer cell lines other than pancreatic cancer.

Accordingly, in another aspect, the present invention is directed to a composition for diagnosing pancreatic cancer, which contains the above-described nucleic acid aptamer of the present invention.

In still another aspect, the present invention is directed to a method of detecting pancreatic cancer using the aptamer of the present invention. The detection method of the present invention comprises bringing the nucleic acid aptamer into contact with a sample selected from among pancreatic tissues, pancreatic cells, blood, serum, plasma, saliva, phlegm and urine. In addition, the sample is not specifically limited and may be any sample containing a pancreatic cancer marker, such as a sample isolated from mammals, preferably humans, and obtainable by minimal invasion, a secreted body fluid, an in vitro culture component, etc.

When the nucleic acid aptamer is brought into contact with a sample, it will bind specifically to a pancreatic cancer marker present in the sample. Thus, pancreatic cancer can be detected by labeling the nucleic acid aptamer with a fluorescent dye or the like, bringing the labeled nucleic acid aptamer into contact with a sample, and determining the presence or absence of the signal of the pancreatic cancer marker.

A pancreatic cancer biomarker can be detected by analyzing a substance of a sample, bound to the nucleic acid aptamer. Thus, in still another aspect, the present invention is directed to a method of detecting a pancreatic cancer cell-specific surface biomarker using the nucleic acid aptamer. For example, a surface biomarker binding specifically to the aptamer can be detected by conjugating biotin to the terminus of the nucleic acid aptamer, allowing the nucleic acid aptamer to bind to a membrane-extracted protein sample from a pancreatic cancer cell line, precipitating the aptamer using streptavidin-conjugated magnetic particles, and then analyzing the aptamer using mass spectrometry.

Meanwhile, the nucleic acid aptamer binding specifically to pancreatic cancer cells or tissues may be immobilized on conventional supports such as beads, particles, dipsticks, fibers, filters, membranes and silane or silicate supports such as glass slides, thereby providing detection sensors which can be used for diagnosis of pancreatic cancer. Thus, in another aspect, the present invention is directed to a sensor for diagnosing pancreatic cancer, having the nucleic acid aptamer binding specifically to pancreatic cells or tissues immobilized thereon.

The above solid support comprises at least one substantially hard surface on which the nucleic acid aptamer can be immobilized by any conventional chemical coupling method. For example, the nucleic acid aptamer can be immobilized on the support surface by conjugating biotin to the terminus of the nucleic acid aptamer to form a conjugate, and immobilizing streptavidin on the support surface to induce the interaction between the biotin and the streptavidin immobilized on the support surface.

Meanwhile the method according to the present invention may be provided in the form of a kit to increase portability. Specifically, in another aspect, the present invention is directed to a kit for diagnosing pancreatic cancer, which contains the nucleic acid aptamer binding specifically to pancreatic cancer cells or tissues. The kit for diagnosing pancreatic cancer may comprise buffer solution and containers for performing detection and analysis, if necessary. The kit for diagnosing pancreatic cancer may take the form of bottles, tubs, sachets, envelops, tubes, ampoules, and the like, which may be formed in part or in whole from plastic, glass, paper, foil, wax, and the like. The sensor container may be equipped with a fully or partially detachable lid that may initially be part of the container or may be affixed to the container by mechanical, adhesive, or other means. The container may also be equipped with a stopper, allowing access to the contents by a syringe needle. The detection kit may comprise an exterior package which may include instructions regarding the use of the components.

In addition, it is known in the art that aptamers binding specifically to cancer cell lines can inhibit the mechanism of cancer to treat the cancer. Thus, the aptamer according to the present invention will bind specifically to pancreatic cancer cells or tissues to inhibit the mechanism of pancreatic cancer. Thus, a person skilled in the art will appreciate that a composition containing the nucleic acid aptamer can provide a composition for treating pancreatic cancer.

The aptamer can be attached to the surface of liposomes or nanoparticles, whereby an anticancer agent, toxin, a cancer growth inhibitor gene or siRNA (small interfering RNA) contained in the liposomes or nanoparticles can be delivered selectively to pancreatic cancer cells. Known pancreatic cancer-specific drugs, cancer cell death-inducing toxin, anticancer agents, known suicide genes such as Herpes simplex virus-thymidine kinase (HSV-TK) or cytosine deaminase (CD), or an siRNA (small interfering RNA) inhibiting the expression of genes playing an important role in the growth and metastasis of pancreatic cells can be attached to the aptamer of the present invention which is then delivered to pancreatic cancer cells. Thus, the nucleic acid aptamer according to the present invention can be provided in the form of a pancreatic cancer-specific drug delivery composition. (aptamer-siRNA conjugate: Silence. 2010 Feb. 1; 1(1):4. "Aptamer-targeted cell-specific RNA interference." Zhou J, Rossi J J.; aptamer-toxin conjugate: Cancer Res. 2006 Jun. 15; 66(12):5989-92. "Aptamer:toxin conjugates that specifically target prostate tumor cells." Chu T C, Marks J W 3rd, Layery L A, Faulkner S, Rosenblum M G, Ellington A D, Levy M.; aptamer-liposome: Chem Commun (Camb). 2010 Jan. 14; 46(2):249-51. Epub 2009 Nov. 23. "A liposome-based nanostructure for aptamer directed delivery." Kang H, O'Donoghue M B, Liu H, Tan W.).

The aptamer in the pharmaceutical composition of the present invention may be used as a pharmaceutically acceptable salt thereof. Also, it may be used alone or in combination with other pharmaceutically active compounds, The pharmaceutical composition according to the present invention can be formulated according to a conventional method. For example, it may be formulated in the form of powders, granules, tablets, capsules, suspensions, emulsions, syrups, agents for external applications, suppositories, and sterile injection solutions. Carriers, excipients and diluents that can be contained in the composition include lactose, glucose, sucrose, sorbitol, mannitol, starch, gum acacia, alginate, gelatin, calcium phosphate, calcium silicate, cellulose, methyl cellulose, microcrystalline cellulose, polyvinylpyrrolidone, water, methylhydroxybenzoate, propylhydroxybenzoate, talc, magnesium stearate and mineral oil.

For formulations, commonly used diluents or excipients such as fillers, expanders, binders, wetting agents, disintegrants and surfactants, etc., are used. Formulations for parenteral administration include sterilized aqueous solutions, non-aqueous solvents, suspensions, emulsions, lyophilized agents, suppositories, etc. Non-aqueous solvents and suspensions may be prepared using propylene glycol, polyethylene glycol, vegetable oils such as olive oil, or injectable esters such as ethyloleate. As a base for suppositories, Witepsol, Macrogol, Tween 61, cacao fat, laurin fat, glycerogelatin, etc. may be used.

The preferred dose of the composition of the present invention can be suitably selected depending on the patient's condition and weight, the severity of disease, the type of drug, and the route and period of administration. The composition of the present invention may be administered by various routes to mammals, including rats, mice, livestock and humans. All routes of administration can be contemplated and include, for example, rectal, intravenous, intramuscular, intrauterine, ntrathecal or intracerebrovascular injections.

EXAMPLES

Hereinafter, the present invention will be described in further detail with reference to examples. It will be obvious to a person having ordinary skill in the art that these examples are illustrative purposes only and are not to be construed to limit the scope of the present invention.

Example 1

Isolation of Aptamer Binding Specifically to Pancreatic Cancer Cell Line 1-1: Preparation of ssRNA Library and Primers for PCR Amplification and cDNA Synthesis A random ssDNA library having the following sequences was chemically synthesized and isolated by PAGE (Genotech Inc., Korea).

```
                                         (SEQ ID NO: 16)
5'-ATA CCA GCT TAT TCA ATT NNN NNN NNN NNN NNN

NNN NNN NNN NNN NNN NNN NNN NNN NAG ATA GTA AGT

GCA ATC T-3'
```

The initial pool contained $7 \times 10^{13}$ molecules. An N40 upstream primer of SEQ ID NO: 17 and an N40 downstream primer of SEQ ID NO: 18 were used for PCR amplification and cDNA synthesis.

```
Upstream primer:
                                         (SEQ ID NO: 17)
5'-GGTAATACGACTCACTATAGGGAGATACCAGCTTATTCAATT-3'

Downstream primer:
                                         (SEQ ID NO: 18)
5'-AGATTGCACTTACTATCT-3'
```

The amplified library was converted into RNA using Durascribe T7 RNA polymerase (Eqicentre). Herein, 2'-F UTP and 2'-F CTP were used in place of UTP and CTP, respectively, whereby U and C in the resulting RNA had 2'-F in place of 2'-OH so as to increase resistance to RNase, thus making it possible to apply the RNA in vivo.

1-2: Selection of Aptamers Binding Specifically to Panc-1 and Capan-1

As shown in FIG. 1, positive selections were performed for the human pancreatic cancer cell lines Panc-1 (American Tissue Culture Collection) and Capan-1 (American Tissue Culture Collection), in which the cell lines were changed for each selection round.

Specifically, the N40 RNA library of Example 1-2 was denatured in a binding buffer (4.5 g/L glucose, 5 mM MgCl$_2$, 0.1 mg/ml yeast tRNA, 1 mg/ml BSA in Dulbecco's PBS) at 95° C. for 5 minutes, and then quenched on ice. Then, 5×10$^6$ cells (Panc-1 and Capan-1 were alternately used) grown into a monolayer were treated with 500 nM of the library at 4° C. for 30 minutes, after the cells were washed twice with a washing buffer (4.5 g/L glucose, 5 mM MgCl$_2$ in Dulbecco's PBS) for 5 minutes each time to remove non-bound sequences. Then, the cells were collected using a washing buffer and heated at 95° C. for 5 minutes, thereby eluting sequences from the cell surface. The eluted sequences were isolated by extraction with PCI (phenol: chloroform: isoamyl alcohol extraction; Bioneer, Korea). The obtained RNAs were subjected to reverse transcription using ImProm-II™ Reverse Transcription System (Promega, USA) and amplified by PCR. The isolated PCR products were subjected to in vitro transcription using T7 polymerase (Ambion, USA).

After the positive selection round has been performed 10 times, two negative selection rounds were performed against the normal pancreatic cell line HPEDE (Ontario Cancer Institute, University of Toronto) while a positive selection round was performed alternately with the negative selection round, as shown in FIG. 1. As a result, a total of 14 positive selection rounds and a total of 2 negative selection rounds were performed.

For selection of aptamers having high affinity and specificity, the number of cells used in each selection round was decreased gradually to 1×10$^6$ cells, the washing time was gradually increased gradually to 15 minutes, and the concentration of yeast tRNA in the binding buffer was increased twice.

The enrichment of bound aptamers was quantified using real-time quantitative PCR (real-time qPCR) and reached a saturated state in the 14$^{th}$ round. For this reason, the products selected in the 14$^{th}$ round were cloned into TA vectors (RBC, Korea). The prepared 50 clones were sequenced using Multialighn software (http://bioinfo.genotoul.fr/multalin/multalin.html), and common sequences between the clones were analyzed. As a result, 15 sequences were obtained from the 50 clones, and RNA aptamer sequences of the present invention, obtained therefrom, are as follows.

SQ1:
(SEQ ID NO: 1)
5'-AUACCAGCUUAUUCAAUU GCCUGAUUAG CGGUAUCACG

AUUACUUACC UUCGUUGCUG AGAUAGUAAGUGCAAUCU-3'

SQ2:
(SEQ ID NO: 2)
5'-AUACCAGCUUAUUCAAUU GCCUGAAAAG CUAUCGCCCA

AUUCGCAGUG AUAUCCUUUA AGAUAGUAAGUGCAAUCU-3'

SQ3:
(SEQ ID NO: 3)
5'-AUACCAGCUUAUUCAAUU GCCUGAAAAC CUGGUCUCUC

UGUCAGCAAA AGAUAGUAAGUGCAAUCU-3'

SQ4:
(SEQ ID NO: 4)
5'-AUACCAGCUUAUUCAAUU GCCUGAGUAG CUGGGUCCGU

CCCCACACAU UACCAUUUGU AGAUAGUAAGUGCAAUCU-3'

SQ5:
(SEQ ID NO: 5)
5'-AUACCAGCUUAUUCAAUU GCCUGAAAAC UGGUGUACCU

CUUUGCCCUA UCUUAUCUGG AGAUAGUAAGUGCAAUCU-3'

SQ6:
(SEQ ID NO: 6)
5'-AUACCAGCUUAUUCAAUU GCCUGAAGAC UGGAUAUACU

CUUAAGCAUU UCUAUAAUCG AGAUAGUAAGUGCAAUCU-3'

SQ7:
(SEQ ID NO: 7)
5'-AUACCAGCUUAUUCAAUU GCCUGAAACU GCUGCAUCGU

CUCCCACGUA UUACACAUGA AGAUAGUAAGUGCAAUCU-3'

SQ8:
(SEQ ID NO: 8)
5'-AUACCAGCUUAUUCAAUU GCCUGAAAAG UUGAACUCCA

AAUACGCGCU G AGAUAGUAAGUGCAAUCU-3'

S49:
(SEQ ID NO: 9)
5'-AUACCAGCUUAUUCAAUU GCCUGAAAAG UGGCCUCCCU

ACAAAGAACU UAUAUCAUCC AGAUAGUAAGUGCAAUCU-3'

S20:
(SEQ ID NO: 10)
5'-AUACCAGCUUAUUCAAUU GCCUGAAAAG UUUAUCCCCC

UUUUAGCGUU UACCAUAAUG AGAUAGUAAGUGCAAUCU-3'

S59:
(SEQ ID NO: 11)
5'-AUACCAGCUUAUUCAAUU ACCUGAAAAC UGGUUUCCGG

CAUCCCGUAU UGCGGCUUUA C AGAUAGUAAGUGCAAUCU-3'

S11:
(SEQ ID NO: 12)
5'-AUACCAGCUUAUUCAAUU GCCUGAAGAG CGAAGUAAAU

CUCUCACUGC GUCACUACA AGAUAGUAAGUGCAAUCU-3'

S52:
(SEQ ID NO: 13)
5'-AUACCAGCUUAUUCAAUU ACCUGAGUAG CGUUUCCCGG

CAUUAUACUA UAAACUU AGAUAGUAAGUGCAAUCU-3'

S68:
(SEQ ID NO: 14)
5'-AUACCAGCUUAUUCAAUU CCUGAAAGUU UGGAUAUCUU

GGCGCUUGAC UAGAAAACUU GAAAUUUGU AGAUAGUAAGU

GCAAUCU-3'

S3:
(SEQ ID NO: 15)
5'-AUACCAGCUUAUUCAAUU CUUAUGUUCA UGCCAGCGCA AUUGCC

AGAUAGUAAGUGCAAUCU-3'

The underlined portions of the 5' end and 3' end of each of the aptamers correspond to the portions introduced for PCR amplification and cDNA synthesis as can be seen in SEQ ID NO: 16, and the nucleic acid sequences of SEQ ID NOS: 1 to 15 commony contain the underlined portions. It was shown that the nucleic acid sequences of SEQ ID NOS: 1 to 14 contain a sequence of CCUGA, and the nucleic acid aptamers SQ2 (SEQ ID NO: 2), SQ3 (SEQ ID NO: 3), SQ5 (SEQ ID NO: 5), SQ8 (SEQ ID NO: 8), S49 (SEQ ID NO: 9) and S20 (SEQ ID NO: 10) particularly contain a commonly conserved sequence of GCCUGAAAA.

Specifically, it can be seen that the sequence of the 5' terminus is conserved in the aptamers of the present invention. Particularly, the aptamers of SEQ ID NOS: 1 to 13 had a conversed sequence such as AGCUUAUUCAAUURC-CUGARDMBBB (R=G or A, D=A, U or G, M=A or C, and B=G, C or U; SEQ ID NO: 35).

Example 2

Measurement of Detection Activity of Aptamer Pool, Selected by Cell-SELEX, for Pancreatic Cancer Cell Line 2-1: Measurement of Binding Affinity for Pancreatic Cancer Cell Line by Real-Time PCR Assay The binding affinities of an initial ssRNA pool and the pools selected in the 5$^{th}$, 10$^{th}$ and 14$^{th}$ rounds of cell-SELEX were measured by a quantitative RT-PCR assay.

Specifically, 1×10$^6$ cells of each of the Capan-1 and Panc-1 cell lines were treated with 100 nM of each of the initial library and the RNA pools. As a control group, a HPEDE cell line that is a normal human pancreatic cell line was used.

Both the in-put aptamer pool and the out-put aptamer pool were used as a template for cDNA synthesis. Diluted cDNA of each round was analyzed by quantitative real-time PCR using a Step-One real-time PCR machine (Applied Biosystems) according to the manufacturer's protocol, and the ratio of the output signal to the input signal was calculated. Herein, the PCR amplification was performed using the primers of SEQ ID NOS: 17 and 18.

Figure 3:
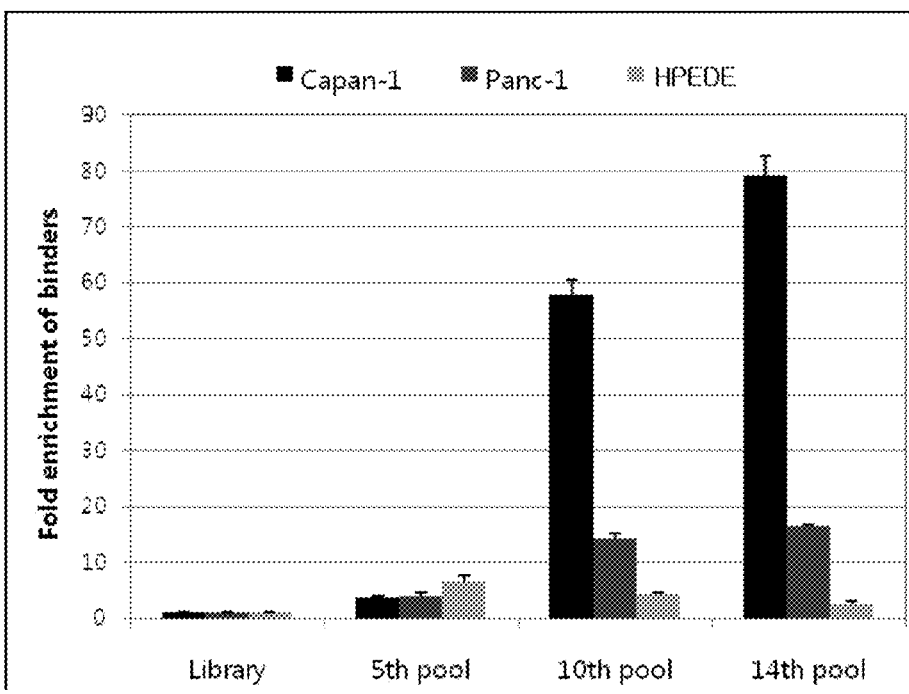
FIG. 3 is a graph showing the results of real-time PCR measurement for the binding affinity of an aptamer pool, selected in each round of cell-SELEX, for a pancreatic cancer cell line.

As a result, as shown in FIG. 3, as the starting material N40 library was subjected to the SELEX selection rounds, the ratio (%) of bound RNA in the aptamer pool obtained in each round gradually increased. However, in the normal pancreatic cell line (HPEDE), the ratio of bound DNA decreased after the negative selection round.

Specifically, according to the cell-SELEX process of the present invention, the enriched aptamer pool could be selected which did bind specifically only to the pancreatic cancer cell lines without recognizing the normal pancreatic cell line.

2-2: Measurement of Binding Affinities for Pancreatic Cancer Cell Line by Fluorescence Detection In order to measure binding affinities by fluorescence detection, a 5' TMARA-labeled downstream primer was used. As a TMARA-labeled 3' primer, 5'-TAMRA-AGAT-TGCACTTACTATCT-3' (SEQ ID NO: 19) was used.

First, the TMARA-labeled primer in an annealing buffer (30 mM HEPES-KOH pH 7.4, 100 mM KCl, 2 mM MgCl$_2$, 50 mM NH4Ac) was mixed with each of the initial RNA library and the aptamer pool of the 14$^{th}$ round at the same concentration, after which each mixture was heat-denatured, cooled, incubated at 37° C. for 20 minutes, whereby it was annealed. Cells grown on the bottom of a Petri dish were cultured in 1 μM of the labeled aptamer pool and a binding buffer (4.5 g/L glucose, 5 mM MgCl$_2$, 0.1 mg/ml yeast tRNA, 1 mg/ml BSA in Dulbecco's PBS) at 37° C. for 20 minutes. Then, the cells were washed rapidly twice with a washing buffer (4.5 g/L glucose, mM MgCl$_2$ in Dulbecco's PBS), and then the fluorescence thereof was detected with a fluorescence microscope (Olympus) at 400× magnification.

Figure 4:
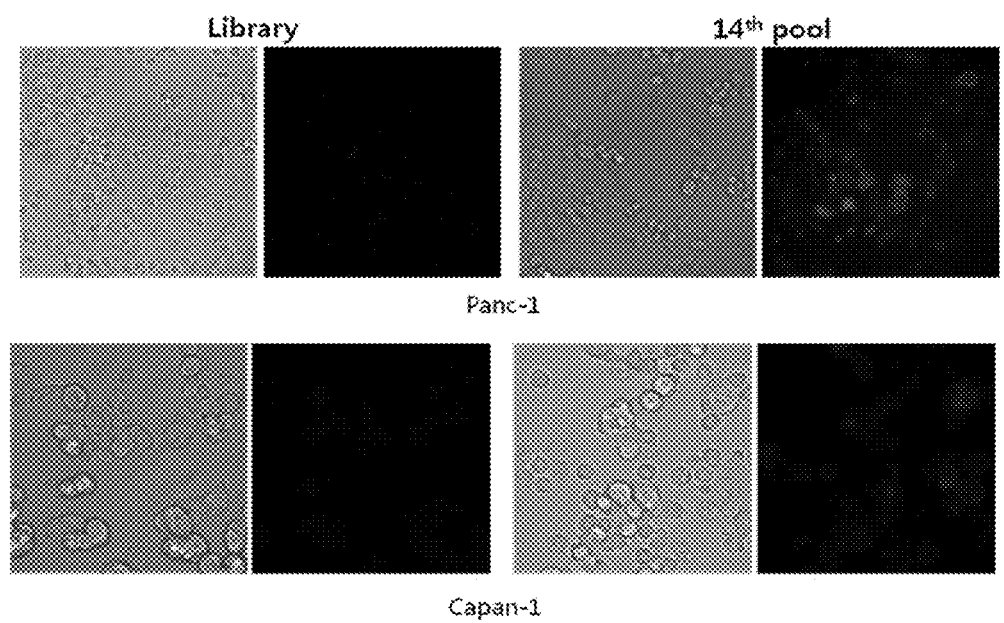
FIG. 4 is a set of photographs showing the results of observing the binding affinity of an aptamer pool, selected in the 14$^{th}$ round of cell-SELEX, by fluorescence detection.

As a result, as shown in FIG. 4, according to the cell-SELEX process of the present invention, the enriched aptamer pool could be selected which did bind specifically only to the pancreatic cancer cell lines without recognizing the normal pancreatic cell line, similar to the results of Example 2-1.

2-3: Measurement of Binding Affinities for Other Cancer Cell Lines

In order to determine the binding affinities of the aptamer pool, finally selected in the 14$^{th}$ round, for other human cancer cell lines, the aptamer pool was subjected to quantitative RT-PCR in Example 2-1 using the pancreatic cancer cell line Capan-1 together with Hela (cervical cancer, American Tissue Culture Collection), T98G (glioblastoma, American Tissue Culture Collection), MDAMB-231 (breast cancer, American Tissue Culture Collection) and Huh7 (liver cancer, American Tissue Culture Collection).

Figure 5:
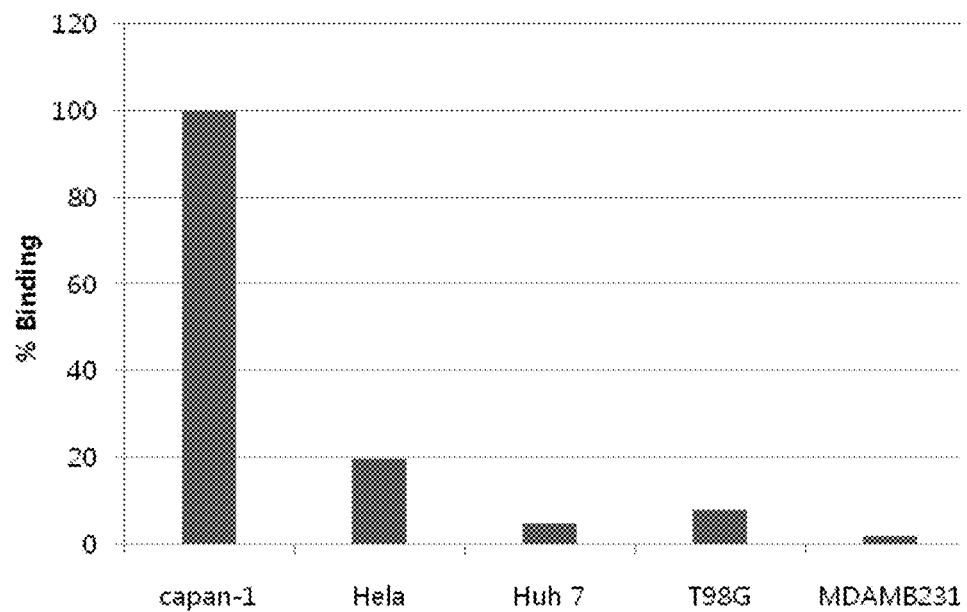
FIG. 5 is a graph showing the results of quantitative real-time RT-PCR measurement for the binding affinity of an aptamer pool, selected in the 14$^{th}$ round of cell-SELEX, for a pancreatic cancer cell line and other cancer cell lines.

As a result, as shown in FIG. 5, it could be seen that the aptamer pool selected in the 14$^{th}$ round could specifically detect the pancreatic cancer cell line without substantially binding to other cancer cell lines.

Example 3

Measurement of Detection Activity of Each Isolated Aptamer for Pancreatic Cancer Cell Line 3-1: Measurement of Binding Affinity for Pancreatic Cancer Cell Line by Real-Time PCR Assay In order to measure the binding affinity of the aptamers, obtained in Example 1, for pancreatic cancer cell lines, the aptamers were subjected to quantitative RT-PCR in the same manner as Example 2-1 using the Capan-1 cell line and the Panc-1 cell line.

Figure 6:
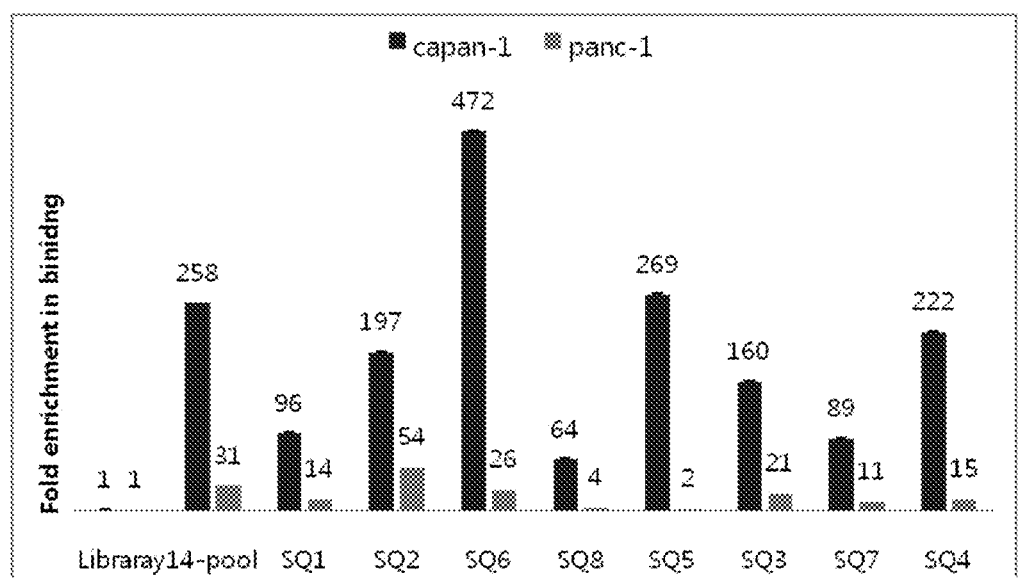
FIG. 6 is a graph showing the results of real-time RT-PCR measurement for the binding affinities of aptamers of the present invention for a pancreatic cancer cell line.

As a result, as shown in FIG. 6, the aptamers had binding affinity for the pancreatic cancer cell lines capan-1 and panc-1. Particularly, SQ2 (SEQ ID NO: 2) and SQ6 (SEQ ID NO: 6) among the aptamers showed very high binding affinities for the two cell lines.

3-2: Measurement of Dissociation Constant (Kd) for Pancreatic Cancer Cell Line by Equilibrium Filtration Method For the SQ2, SQ4, SQ6 and SQ8 aptamers and the SQ1 aptamer showing a high copy number, a binding assay was performed an equilibrium filtration method. Specifically, 0.5×10$^6$ cells of each of the Pan1 and Capan-1 cell lines were incubated with 1 nM to 1 μM of each aptamer, and then subjected to a binding reaction in the same manner as Example 1. The bound aptamers were quantified by quantitative RT-PCR in the same manner as Example 2-1.

In order to calculate dissociation constant, using Sigmaplot 10.0 software and the following equation, the percent of bound pancreatic cancer cells versus ssRNA concentration was plotted, and the data points were fitted into nonlinear regression analysis:

$$y = (B_{max} \cdot ssRNA)/(K_d + ssRNA)$$

wherein y is the degree of saturation, $B_{max}$ is the number of maximum binding sites, and $K_d$ is dissociation constant.

Figure 7:
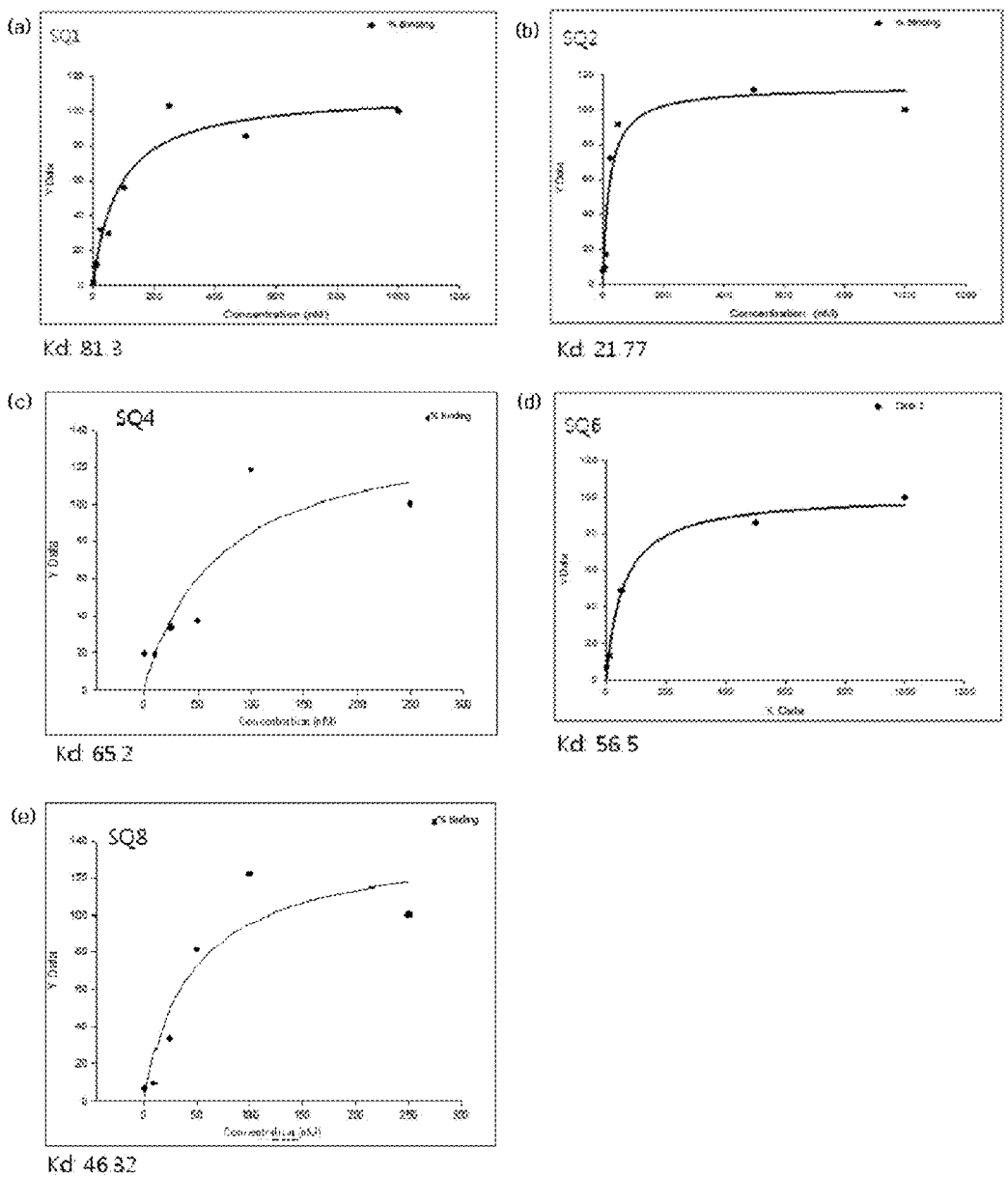
FIG. 7 is a set of graphs showing the binding affinities of aptamers of the present invention for Capan-1 cell line.
Figure 8:
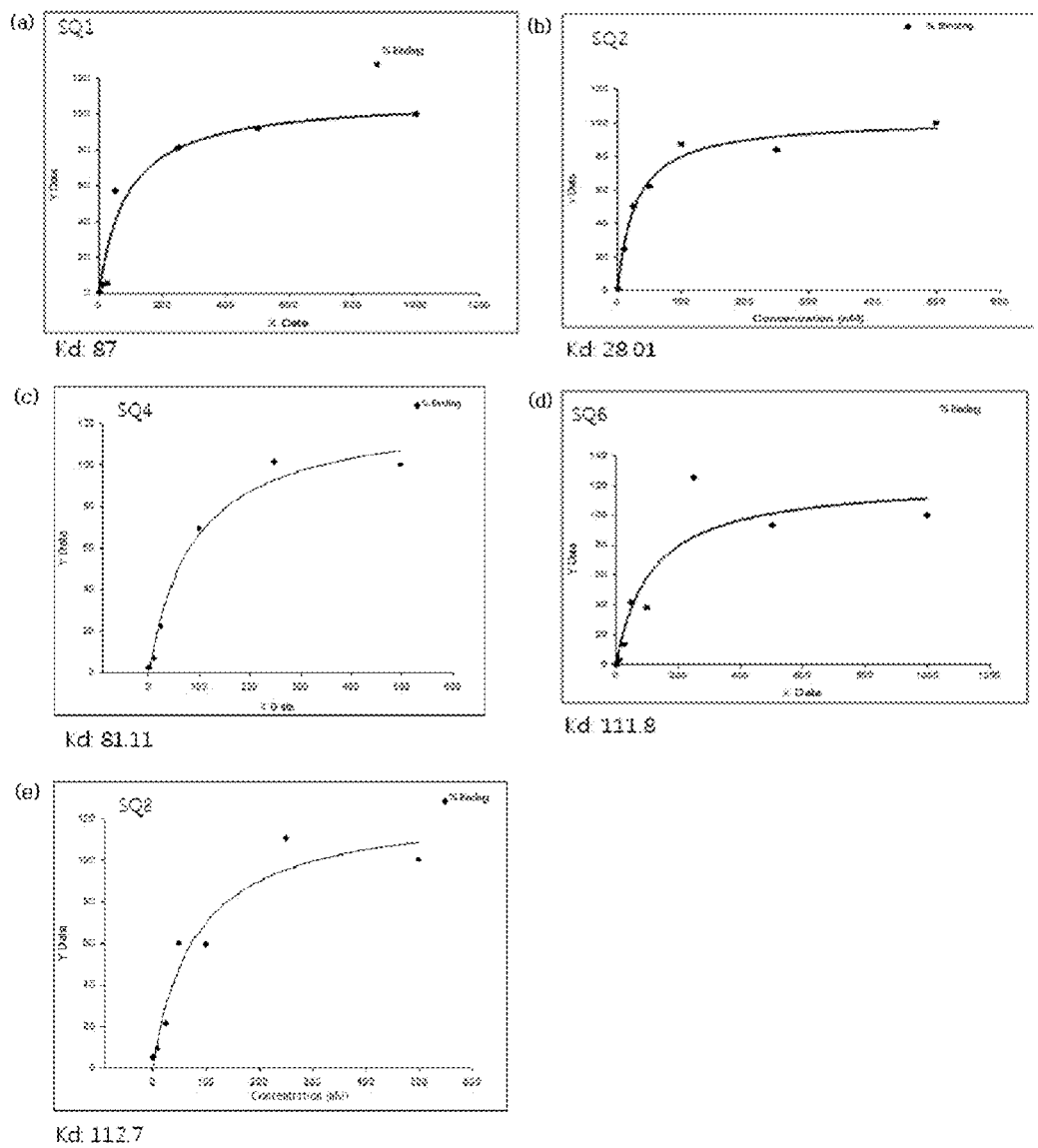
FIG. 8 is a set of graphs showing the binding affinities of aptamers of the present invention for Panc-1 cell line.

As a result, as shown in FIG. 7 (Capan-1) and FIG. 8 (Panc-1), the aptamers showed strong binding affinity for the pancreatic cancer cell lines. Particularly, SQ2 of the SEQ ID NO: 2 had the highest affinity for the cancer cell lines.

3-3: Measurement of Binding Affinity for Pancreatic Cancer Cell Lines by Fluorescence Detection In order to measure the binding affinities of the SQ2 and SQ6 aptamers and the SQ1 aptamer showing a high copy number for the pancreatic cancer cell lines, the detection of fluorescence was performed using the 5' TMARA-labeled downstream primer in the same manner as Example 2-2.

Figure 9:
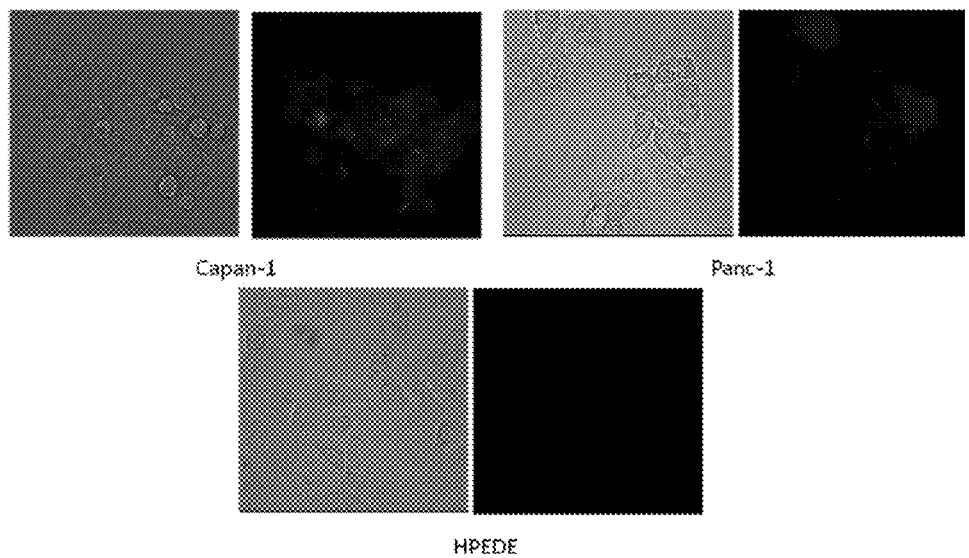
FIG. 9 is a set of photographs showing the results of observing the binding affinities of aptamer SQ1 of the present invention for a pancreatic cancer cell line and a normal cell line by fluorescence detection.
Figure 10:
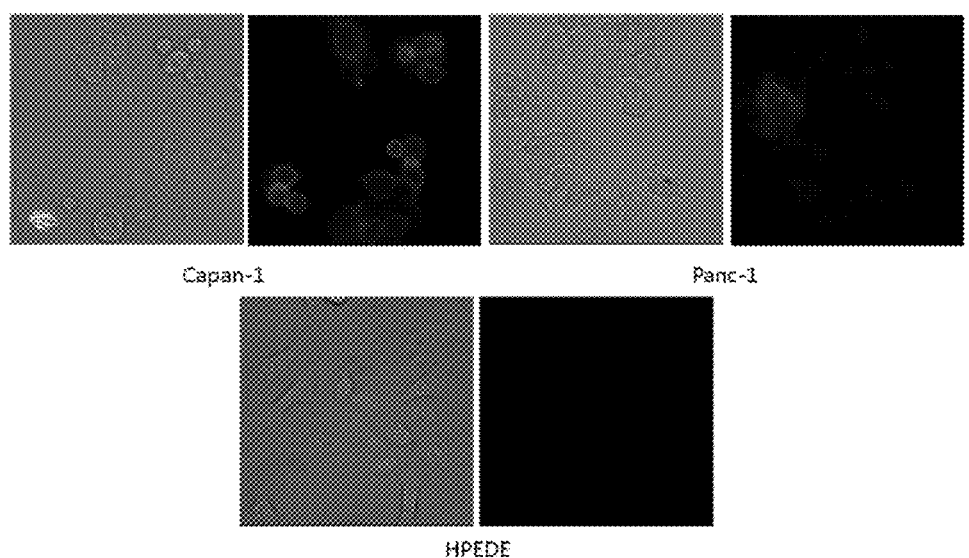
FIG. 10 is a set of photographs showing the results of observing the binding affinities of aptamer SQ2 of the present invention for a pancreatic cancer cell line and a normal cell line by fluorescence detection.
Figure 11:
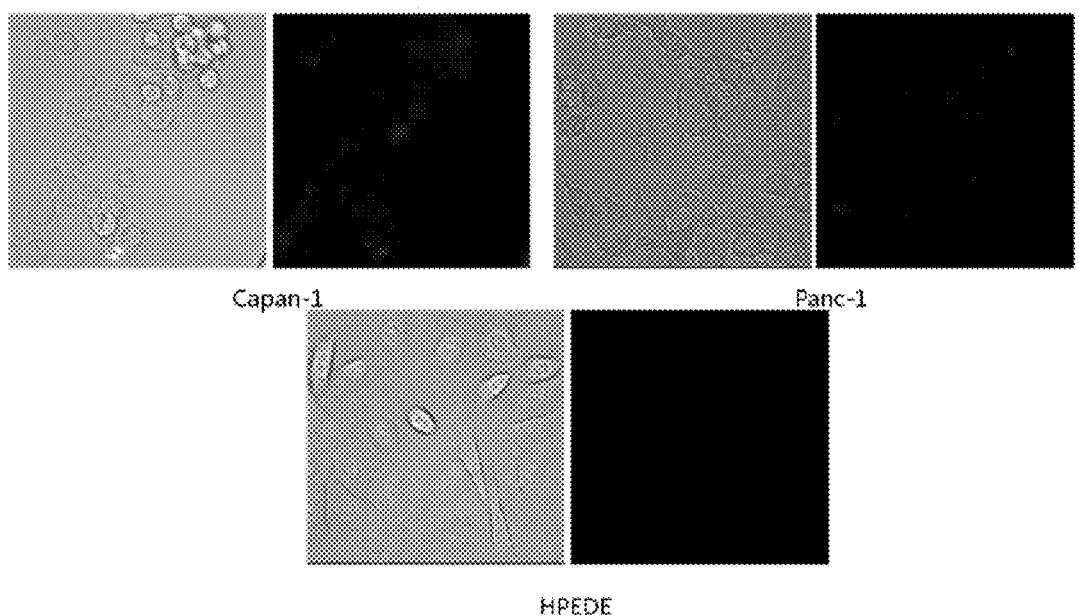
FIG. 11 is a set of photographs showing the results of observing the binding affinities of aptamer SQ6 of the present invention for a pancreatic cancer cell line and a normal cell line by fluorescence detection.
Figure 12:
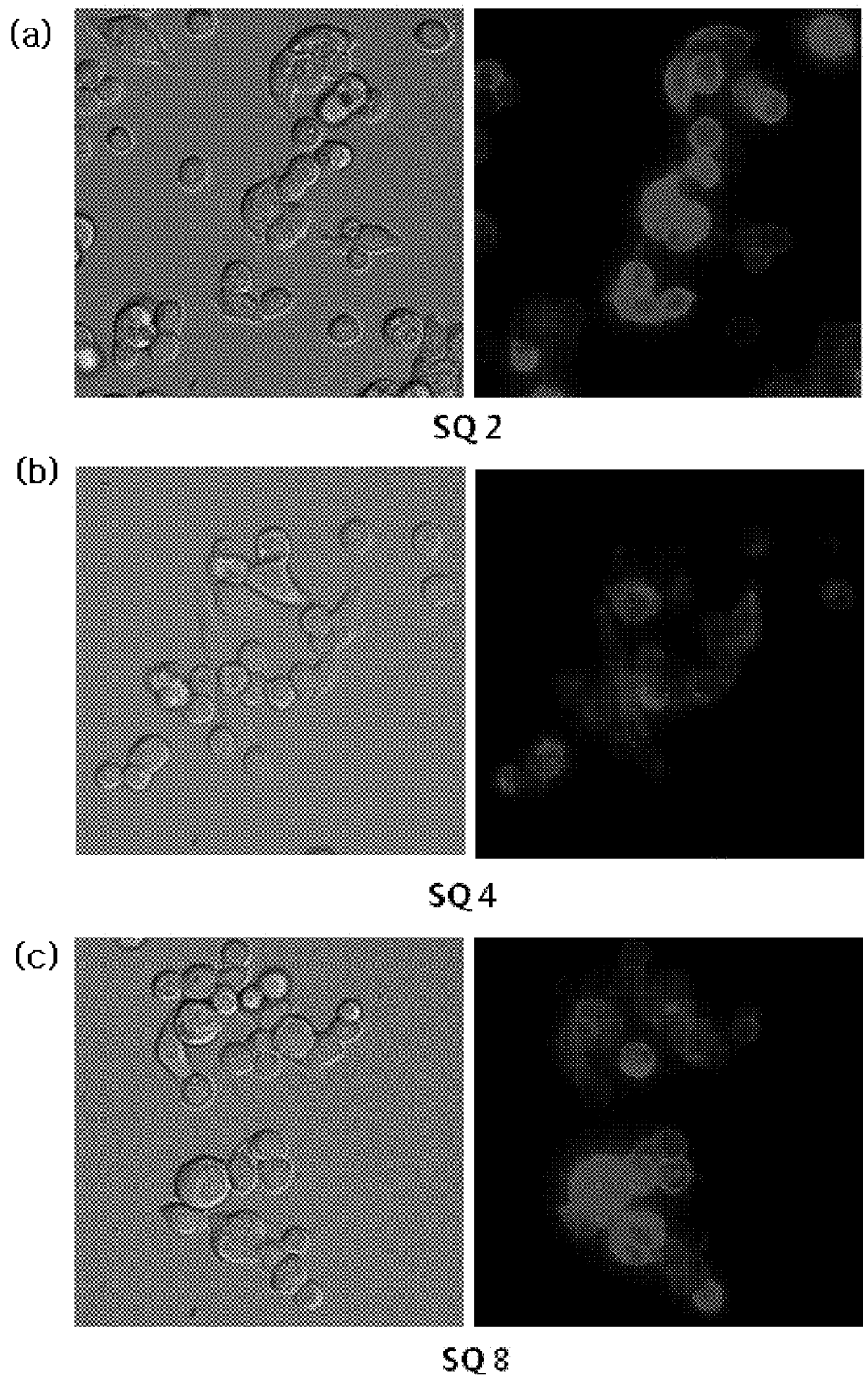
FIG. 12 is a set of photographs showing the results of observing the binding affinities of aptamers SQ2, SQ4 and SQ8 of the present invention for the pancreatic cancer cell line Capan-1 by fluorescence detection.
Figure 14:
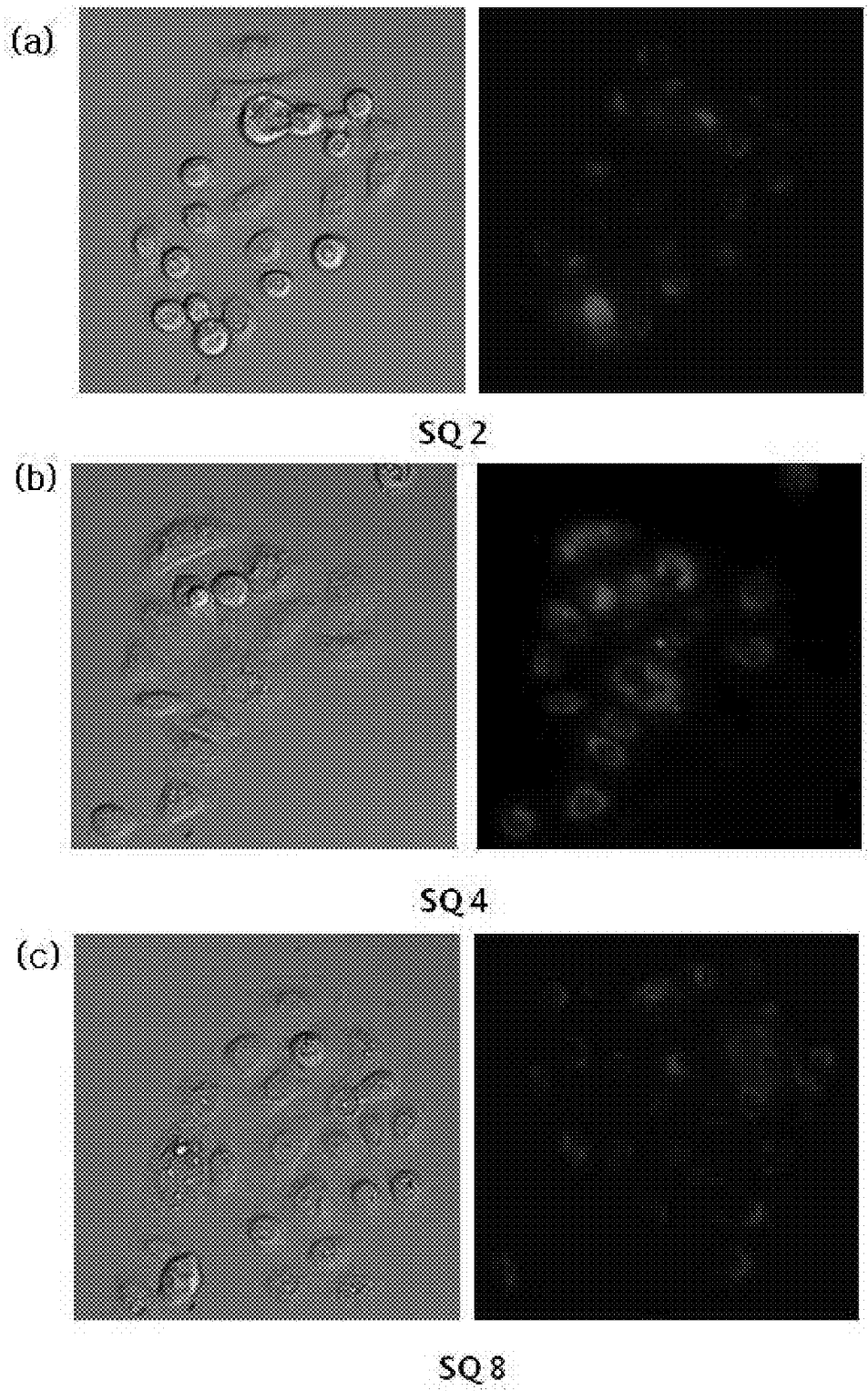
FIG. 14 is a set of photographs showing the results of observing the binding affinities of aptamers SQ2, SQ4 and SQ8 of the present invention for pancreatic cancer cell line Aspc-1 by fluorescence detection.
Figure 15:
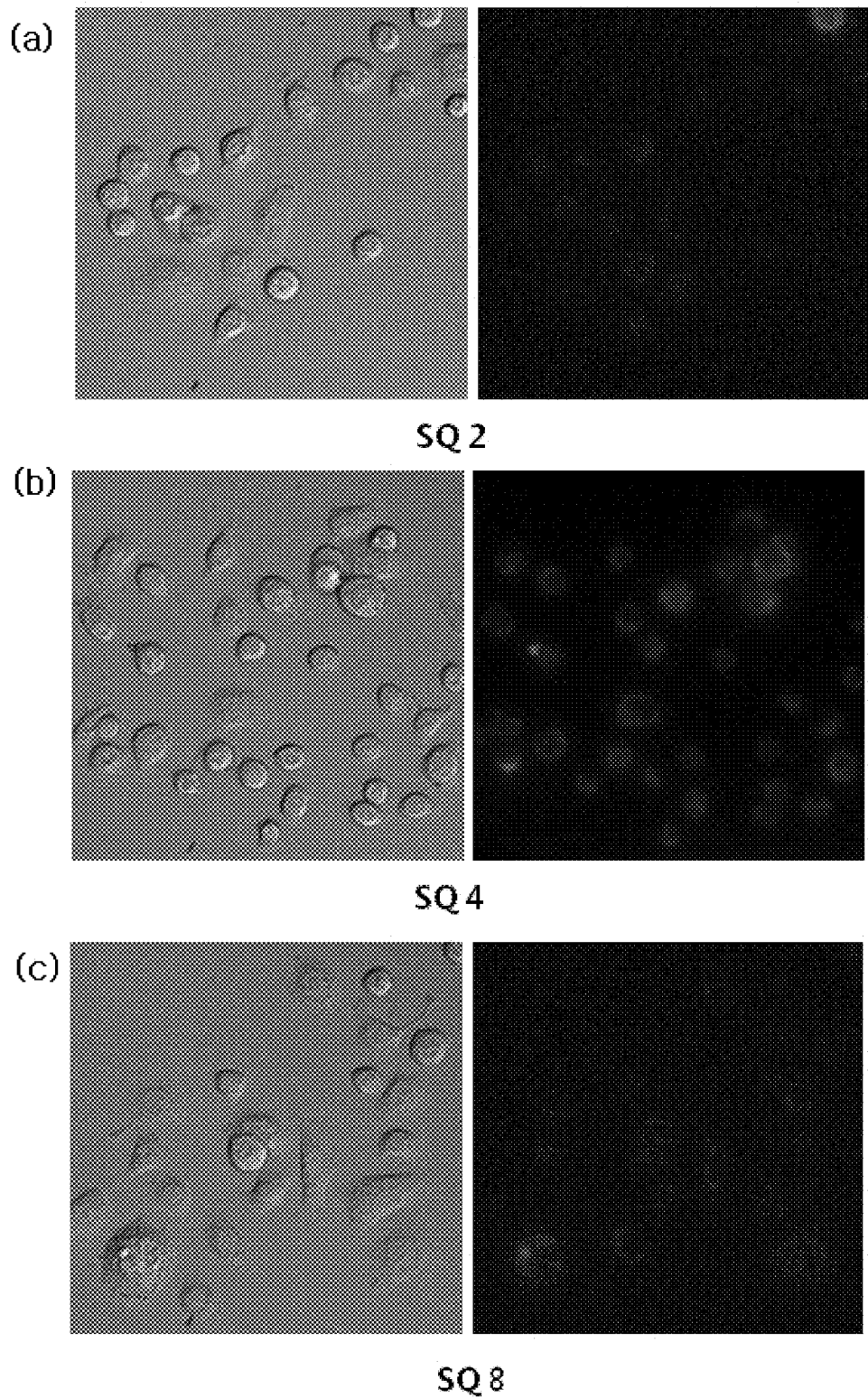
FIG. 15 is a set of photographs showing the results of observing the binding affinities of aptamers SQ2, SQ4 and SQ8 of the present invention for pancreatic cancer cell line Bxpc-3 by fluorescence detection.

As a result, as shown in FIGS. 9 to 11, all the signal of SQ1 (FIG. 9), SQ2 (FIG. 10) and SQ6 (FIG. 11) were not observed in the normal cell line HPEDE, but were observed in the pancreatic cell lines Capan-1 and Panc-1. This suggests that the aptamers according to the present invention can specifically detect the pancreatic cancer cell lines, and thus can be advantageously used as compositions for diagnosing pancreatic cancer. Particularly, it was shown that the aptamers could also detect the pancreatic cancer cell line Panc-1 that indicates an early stage of pancreatic cancer, suggesting that the aptamers can be used for early diagnosis of pancreatic cancer.

Example 4

Measurement (1) of Detection Activity of Each Isolated Aptamer for Various Pancreatic Cancer Cell Lines In order to examine whether the SQ2, SQ4 and SQ8 aptamers can specifically detect pancreatic cancer cell lines other than Panc-1 and Capan-1, the detection of fluorescence in pancreatic cancer cell lines of Bxpc-3, Aspc-1, Miacapa-1 and Hapaf-2 was performed using the 5' TMARA-labeled downstream primer as in Example 2-2.

Figure 17:
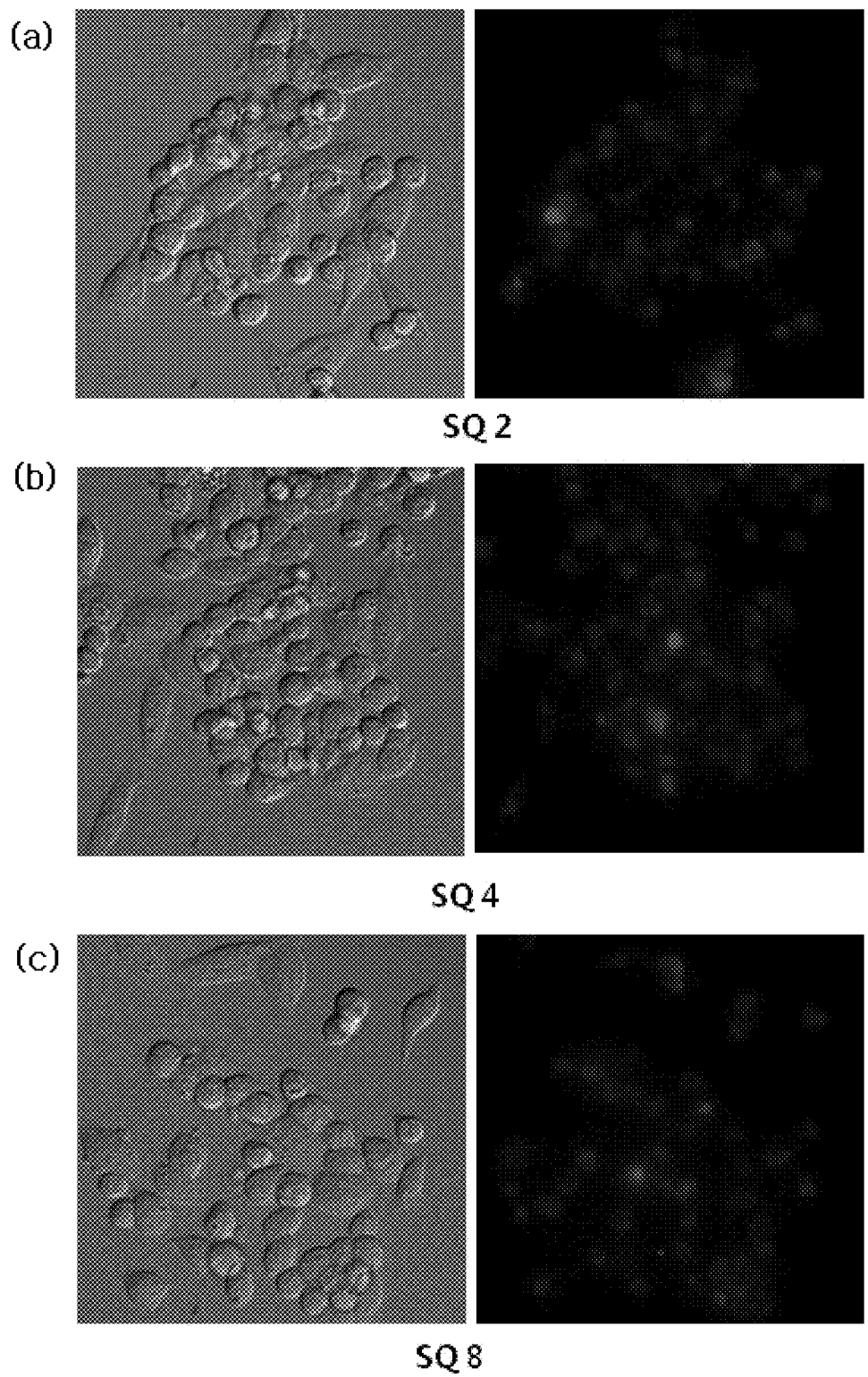
FIG. 17 is a set of photographs showing the results of observing the binding affinities of aptamers SQ2, SQ4 and SQ8 of the present invention for pancreatic cancer cell line Miacapa-2 by fluorescence detection.

As a result, as shown in FIGS. 12 to 17, the signals of the aptamers could be observed not only in the pancreatic cancer cell lines Capan-1 (FIG. 12) and Pan-1 (FIG. 13) used in the positive selection rounds, but also in the other pancreatic cancer cell lines Aspc-1 (FIG. 14), Bxpc-3 (FIG. 15), Hapaf-∥ (FIG. 16) and Miacapa-2 (FIG. 17). Specifically, it was found that the aptamers according to the present invention can be used to detect not only the pancreatic cancer cell lines used in the positive selection process, but also other pancreatic cancer cell lines, suggesting that the aptamers can be effectively used for diagnosis of pancreatic cancer cell.

Example 5

Measurement (2) of Detection Activity of Each Isolated Aptamer for Pancreatic Cancer Cell Lines 5-1: Measurement of Binding Affinity for Pancreatic Cancer Cell Lines by Fluorescence Detection In order to measure binding affinity by fluorescence detection, the detection of fluorescence was performed using the 5' TMARA-labeled downstream primer of SEQ ID NO: 19.

First, the TMARA-labeled primer in an annealing buffer (30 mM HEPES-KOH pH 7.4, 100 mM KCl, 2 mM MgCl$_2$, 50 mM NH4Ac) was mixed with each of the SQ1 to SQ8 aptamers at the same concentration, after which each mixture was heat-denatured, cooled, incubated at 37° C. for 20 minutes, whereby it was annealed. Cells grown on the bottom of a Petri dish were cultured in 100 nM of the 3'-TAMRA-labeled labeled aptamer and a binding buffer (4.5 g/L glucose, 5 mM MgCl$_2$, 0.1 mg/ml yeast tRNA, 1 mg/ml BSA in Dulbecco's PBS) at 37° C. for 20 minutes. Then, the cells were washed rapidly twice with a washing buffer (4.5 g/L glucose, 5 mM MgCl$_2$ in Dulbecco's PBS), and then the fluorescence thereof was detected with a fluorescence microscope (Olympus) at 400× magnification.

Figure 18:
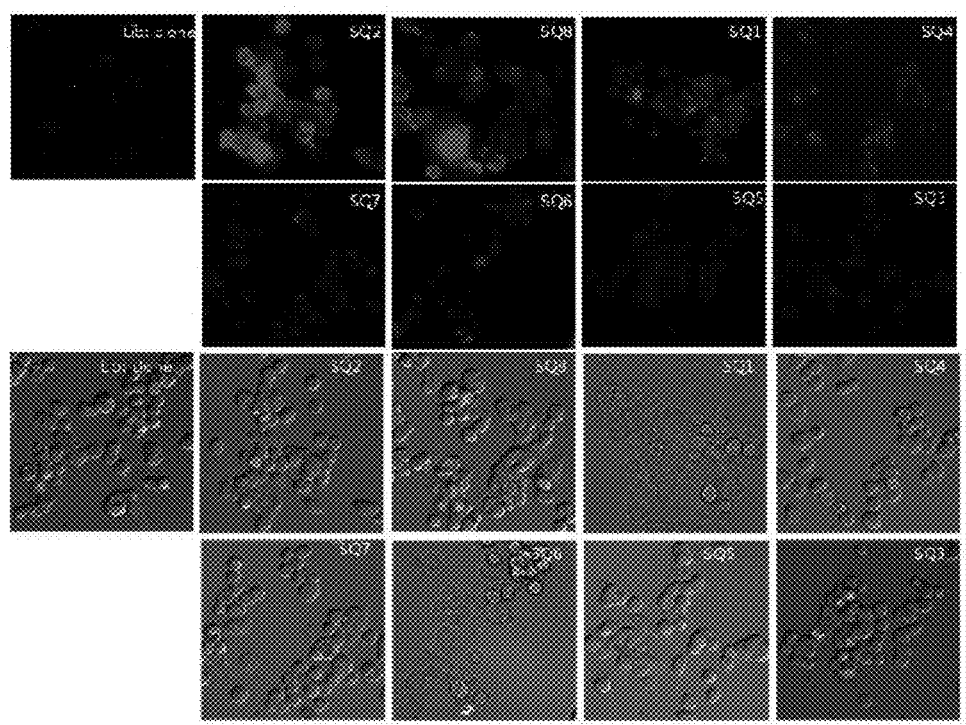
FIG. 18 is a set of photographs showing the results of observing the binding affinities of aptamers SQ1 to SQ8 of the present invention for the pancreatic cancer cell line Capan-1 by fluorescence detection.
Figure 19:
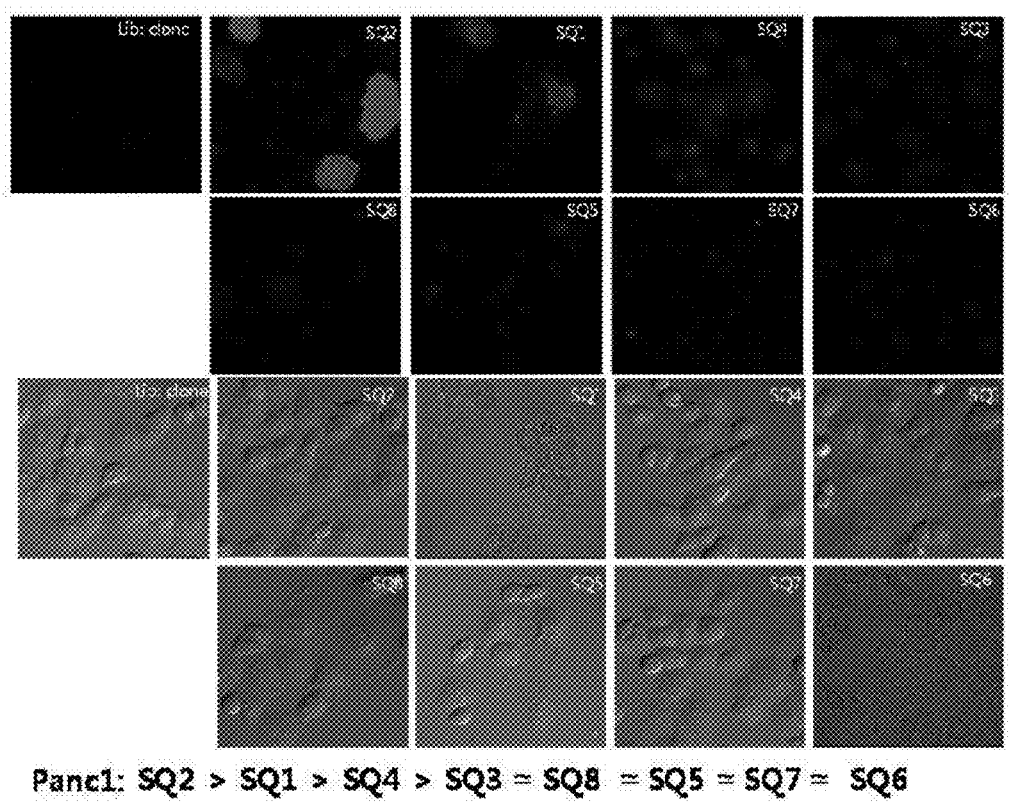
FIG. 19 is a set of photographs showing the results of observing the binding affinities of aptamers SQ1 to SQ8 of the present invention for pancreatic cancer cell line Panc-1 by fluorescence detection.

As a result, as can be seen in FIGS. 18 and 19, the aptamers SQ1 to SQ8 all had binding affinities for the pancreatic cancer cell lines Capan-1 and Panc 1, and particularly, the SQ2 aptamer had the highest binding affinity.

5-2: Measurement of Binding Affinity for Pancreatic Cancer Cell Lines by Real-Time PCR Assay In addition, in order to measure the binding affinities of the SQ1 to SQ8 aptamers for pancreatic cancer cell lines, a binding assay was performed by an equilibrium filtration method in the same manner as Example 3-2, and dissociation constant was determined.

TABLE 1

Binding affinities (Kd) of aptamers detected by qRT-PCR

| Aptamer | Pan-1 (Kd: nM) | Capan-1 (Kd: nM) |
|---------|----------------|------------------|
| SQ1 | 82 | 78 |
| SQ2 | 26.15 | 24.7 |
| SQ3 | 57 | 5.2 |
| SQ4 | 100 | 69 |
| SQ5 | 26 | 16 |
| SQ6 | 150 | 56 |
| SQ7 | 23 | 5.6 |
| SQ8 | 89 | 46 |

As a result, as shown in table 1, in the same manner as Example 5-1, the aptamers SQ1 to SQ8 all showed binding affinities for the pancreatic cancer cell lines, and particularly, SQ1, SQ2, SQ4, SQ6 and SQ8 showed high affinities for both the pancreatic cancer cell lines Pan-1 and Capan-1.

Example 6

Measurement of Binding Affinities of Truncated Aptamers

The SQ2 aptamer shown to have the highest affinity in the detection of fluorescence was truncated as follows, and then the binding affinities of the truncated aptamers for the pancreatic cancer cell line Capan-1 were measured:

SQ2 down truncated (SEQ ID NO: 36): comprising a deletion of 18 nts in the 3' terminus of the SQ2 aptamer; SQ2 up truncated (SEQ ID NO: 37): comprising a deletion of 18 nts in the 5' terminus of the SQ2 aptamer; SQ2 6-58 (SEQ ID NO: 38): comprising a deletion of 18 nts in the 3' terminus and a deletion of 5 nts in the 5' terminus of the SQ2 aptamer; SQ2 6-50 (SEQ ID NO: 39): comprising a deletion of 26 nts in the 3' terminus and a deletion of 5 nts in the 5' terminus of the SQ2 aptamer; SQ2 1-50 (SEQ ID NO: 40): comprising a deletion of 26 nts in the 3' terminus of the SQ2 aptamer; and SQ2 6-30 (SEQ ID NO: 41): comprising a deletion of 51 nets in the 3' terminus and a deletion of 5 nts in the 5' terminus of the SQ2 aptamer.

SQ2 full length (SEQ ID NO: 2):
5'-AUACCAGCUUAUUCAAUUGCCUGAAAAGCUAUCGCCCAAUUCGC AGUGAUAUCCUUUAAGAUAGUAAGUGCAAUCU-3' (76nts)

SQ2 down truncated (SEQ ID NO: 36):
5'-AUACCAGCUUAUUCAAUUGCCUGAAAAGCUAUCGCCCAAUUCGC AGUGAUAUCCUUUA-3' (58nts)

SQ2 up truncated (SEQ ID NO: 37):
5'-GCCUGAAAAGCUAUCGCCCAAUUCGCAGUGAUAUCCUUUAAGAU

AGUAAGUGCAAUCU-3' (58nts)

SQ2 6-58 (SEQ ID NO: 38):
5'-AGCUUAUUCAAUUGCCUGAAAAGCUAUCGCCCAAUUCGCAGUGA

UAUCCUUUA-3' (53nts)

SQ2 6-50 (SEQ ID NO: 39):
5'-AGCUUAUUCAAUUGCCUGAAAAGCUAUCGCCCAAUUCGCAGUGA

U-3' (45nts)

-continued

SQ21-50 (SEQ ID NO: 40):
5'-AUACCAGCUUAUUCAAUUGCCUGAAAAGCUAUCGCCCAAUUCGC
AGUGAU-3' (50nts)

SQ2 6-30 (SEQ ID NO: 41):
5'-AGCUUAUUCAAUUGCCUGAAAAGCU-3' (25nts)

The SQ2 aptamer has a site binding to the T7 promoter. In order to aptamers modified by 2-F and truncated as described above, the aptamers were annealed with T7 promoter and subjected to in vitro transcription using DuraScribe® T7 transcription kit (EPICENTRE® Biotechnologies). Then, the binding affinities of the aptamers for Capan-1 were measured in the same manner as Example 3-2 and compared with the binding affinity of the SQ2 aptamer.

Figure 20:
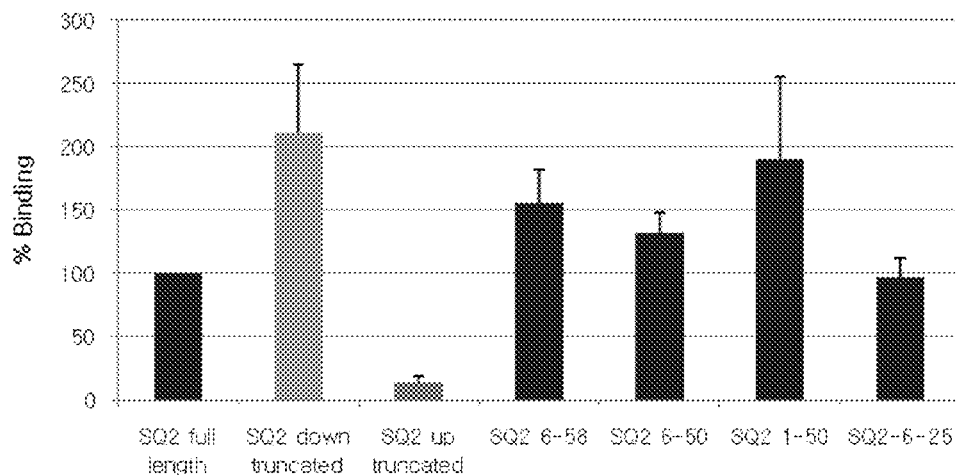
FIG. 20 shows the relative ratio of the binding affinities of aptamers, obtained by truncating the SQ2 aptamer, for a pancreatic cancer cell line.

As a result, as shown in FIG. 20, the aptamers obtained by truncating the SQ2 aptamer sequence still had affinity for the pancreatic cancer cell line, and particularly, SO2 down truncated (SEQ ID NO: 36) obtained by truncating the 3' terminus of the SQ2 aptamer showed a binding affinity higher than the SQ2 aptamer. Also, the aptamers, with or without a deletion of 5 nts in the 5' terminus of the SQ2 aptamer, showed a binding affinity similar to or higher than the SQ2 aptamer. However, SQ2 up truncated (SEQ ID NO: 37) comprising a deletion of 18 nts in the 5' terminus of the SQ2 aptamer showed relatively low binding affinity for the pancreatic cancer line Capan-1. Meanwhile, the above test results suggest that even the sequence having a short length of 25 nts, that is, AGCUUAUUCAAUUGCCUGAAAAGCU (SEQ ID NO: 41), shows high binding affinity for the pancreatic cancer cell line.

Figure 21:
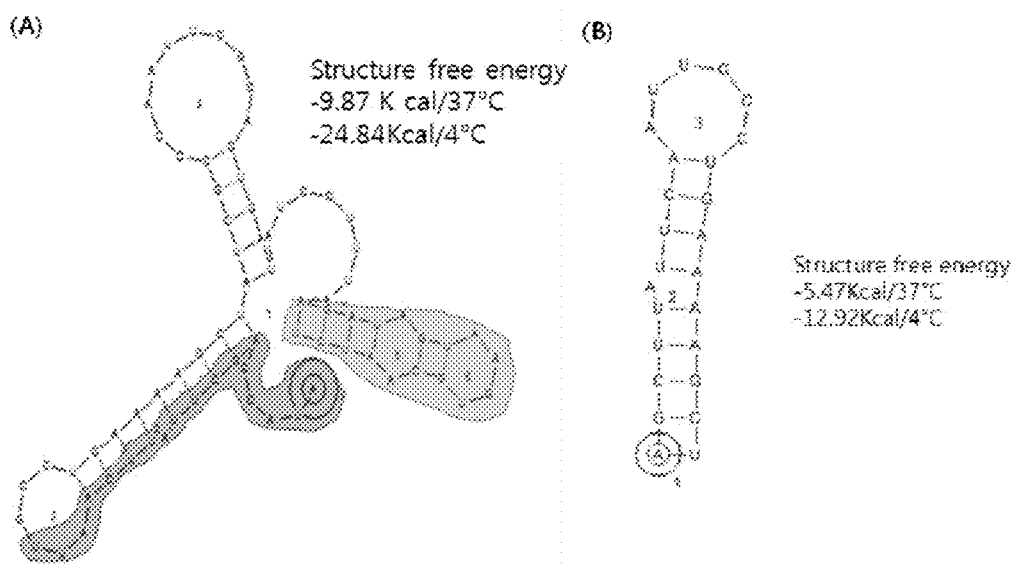
FIG. 21 shows the secondary structure of the SQ2 aptamer (FIG. 21A) and the secondary structure of SQ2 6-30 (FIG. 21B).

Additionally, as shown in FIG. 21, the secondary structure of full-length SQ2 (SEQ ID NO: 2) (FIG. 21A) was compared with the secondary structure of SQ2 6-30 (SEQ ID NO: 41) (FIG. 21B). As a result, it can be seen that stems 1 and 2 and loop 3 in the secondary structure of the SQ2 aptamer plays an important role. In FIG. 21, the structure was predicted using RNA draw 1.1 software, and the 2D radical structure and the free energy were calculated at 4° C. and 37° C., and the 5' terminus of the sequence was indicated by a concentric circle.

Such results indicate that the conserved sequence in the 5' terminus of the aptamer according to the present invention is important. The aptamers of SEQ ID NOS: 1 to 15, isolated according to the present invention, have a conserved sequence in the 5' terminus, and particularly, the aptamers of SEQ ID NOS: 1 to 13 have a conserved sequence such as AGCUUA-UUCAAUURCCUGARDMBBB (R=G or A, D=A, U or G, M=A or C, and B=G, C or U; SEQ ID NO: 35).

Accordingly, it can be seen that an aptamer comprising any one nucleic acid sequence selected from nucleic acids comprising the nucleic acid sequence of SEQ ID NO: 35 can bind specifically to pancreatic cancer cells or tissues.

Example 7

Measurement of Detection Activities of Truncated Aptamers for Pancreatic Cancer Cell Lines and Other Cancer Cell Lines 7-1: Measurement of Fluorescence Activity for Pancreatic Cancer Cell Line by Fluorescence Detection As described above, SQ2 6-30 (SEQ ID NO: 41) showed high binding affinity for the pancreatic cancer cell line, even though it had a length of only 25 nts. In order to measure the binding affinities of SQ2 6-30 for the pancreatic cancer cell lines Capan-1, Panc-1 and HPAF-II (ATCC), the detection of fluorescence in the cancer cell lines was performed using the 5' TMARA-labeled downstream primer in the same manner as Example 2-2.

Figure 22:
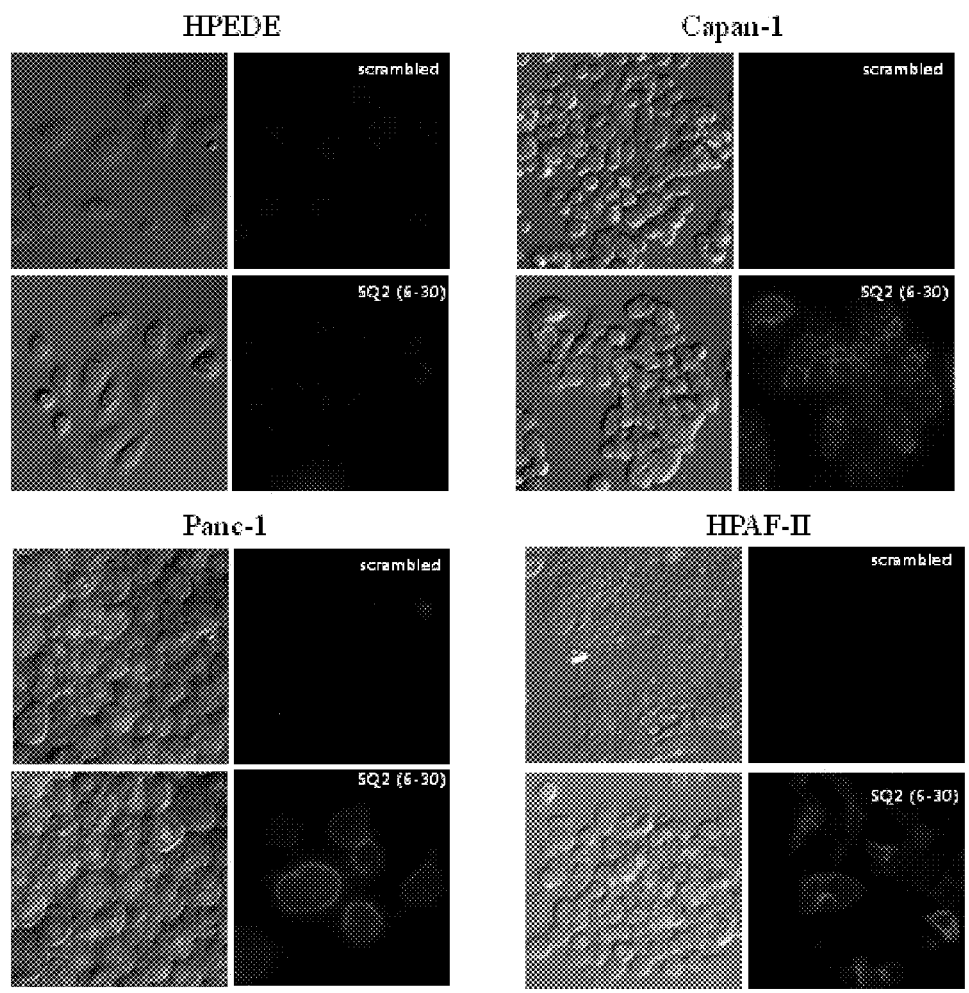
FIG. 22 is a set of photographs showing the results of observing the binding affinities of SQ2 6-30 for a pancreatic cancer cell line and a normal cell line by fluorescence detection.

As a result, as can be seen in FIG. 22, the signal of the SQ2 6-30 (SEQ ID NO: 41) aptamer was not observed in the normal cell line HPEDE, but was observed in the pancreatic cancer cell lines Capan-1 and Panc-1.

Thus, it can be seen that the truncated aptamers can specifically detect pancreatic cancer cell lines, and thus can be effectively used as compositions for diagnosing pancreatic cancer. Particularly, the truncated aptamers can also detect the pancreatic cancer cell line Panc-1 that indicates an early stage of pancreatic cancer, suggesting that they can be used for early diagnosis of pancreatic cancer.

7-2: Measurement of Fluorescence Activity for Other Cancer Cell Lines by Fluorescence Detection In order to examine whether the aptamer according to the present invention can specifically detect only pancreatic cancer, the detection of fluorescence in other cancer cell lines SK-BR-3 (Human Breast cancer, ATCC), LnCap (Human Prostate cancer, ATCC), Hep G2 (Human Liver carcinoma, ATCC), Hela (ATCC), A549 (Human Lung Adenocarcinoma, ATCC), SK-N-SH (Human Neuroblastoma, ATCC), T98G (ATCC) and Bend-3 (Mouse Endothelial cells, ATCC)) was performed using the 5' TMARA-labeled downstream primer in the same manner as Example 2-2.

TABLE 2

| Cell line | Origin | SQ2 6-30 Binding |
|---|---|---|
| SK-BR-3 | Human Breast cancer | − |
| LnCap | Human Prostrate cancer | − |
| Hep G2 | Human Liver carcinoma | − |
| Hela | Human Cervical cancer | ± |
| A549 | Human Lung Adenocarcinoma | − |
| SK-N-SH | Human Neuroblastoma | − |
| T98G | Human Glioblastoma | − |
| Bend-3 | Mouse Endothelial cells | − |

Figure 23:
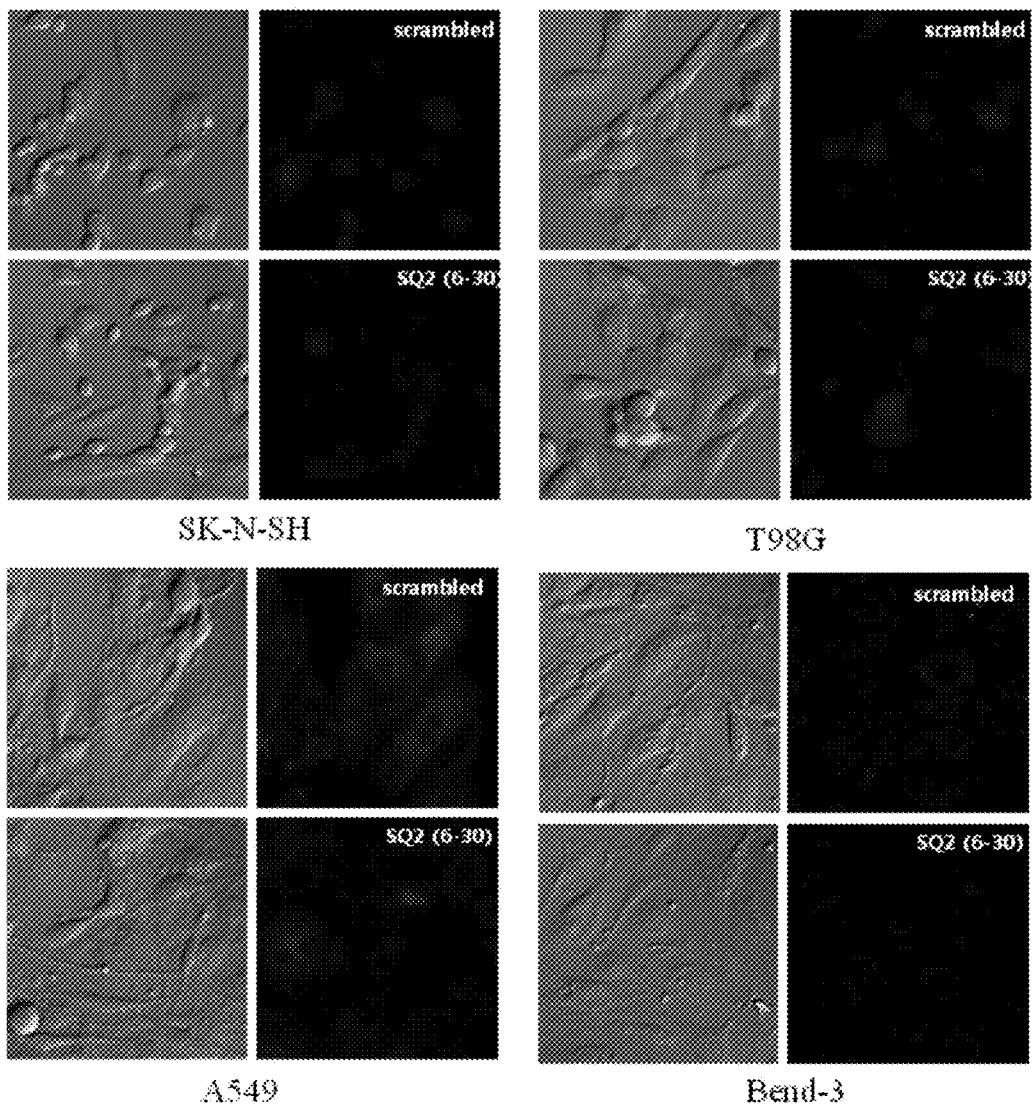
FIG. 23 is a set of photographs showing the results of observing the binding affinities of SQ2 6-30 for the non-pancreatic cancer cell lines SK-N-SH, T98G, A549 and Bend-3, by fluorescence detection.
Figure 24:
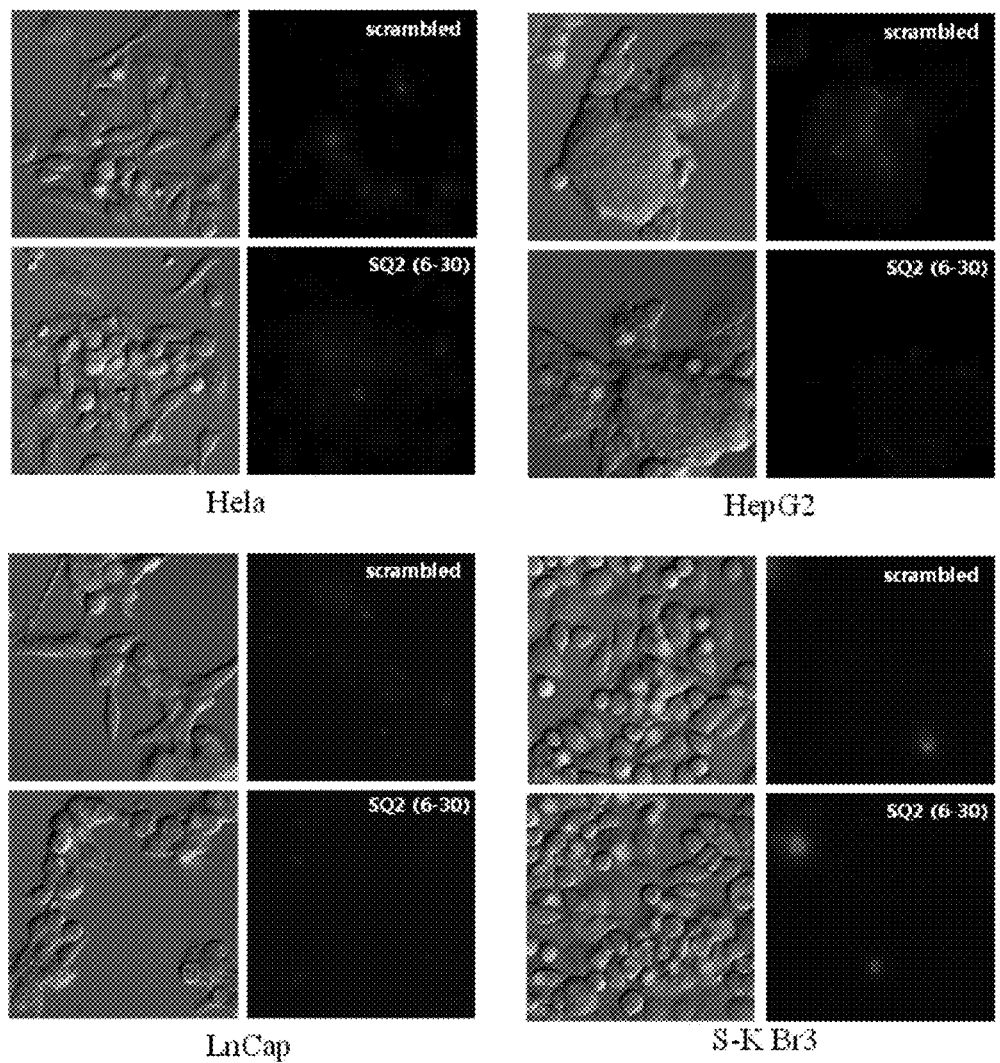
FIG. 24 is a set of photographs showing the results of observing the binding affinities of SQ2 6-30 for the non-pancreatic cancer cell lines Hela, Hep G2, LnCap, SK-Br3, T98G, A549 and Bend-3, by fluorescence detection.

As a result, as can be seen in FIGS. 23 and 24 and Table 2, SQ2 6-30 (SEQ ID NO: 41) did not recognize cancer cell lines other than pancreatic cancer cell lines. This suggests that the aptamer according to the present invention can be used for the specific diagnosis and treatment of pancreatic cancer.

INDUSTRIAL APPLICABILITY

As described above, the nucleic acid aptamer according to the present invention can bind specifically only to pancreatic cancer cells or tissues without binding to normal pancreatic cancer tissue, and thus can be effectively used as a composition for diagnosing and treating pancreatic cancer. In addition, the nucleic acid aptamer can detect not only the terminal pancreatic cancer cell line Capan-1, but also the early pancreatic cancer cell line Panc-1, and thus can be used for early diagnosis of pancreatic cancer, thereby contributing to increasing the survival rate of pancreatic cancer patients.

Although the present invention has been described in detail with reference to the specific features, it will be apparent to those skilled in the art that this description is only for a preferred embodiment and does not limit the scope of the present invention. Thus, the substantial scope of the present invention will be defined by the appended claims and equivalents thereof.

What is claimed is:

1. A nucleic acid aptamer of 25-100 nts, which comprises SEQ ID NO: 35, and is capable of binding specifically to pancreatic cancer cells or tissues, wherein U in the nucleic acid sequence is T if the nucleic acid aptamer is DNA.

2. The nucleic acid aptamer of claim 1, wherein a length of the nucleic acid aptamer is 25-85 nts.

3. The nucleic acid aptamer of claim 1, wherein the nucleic acid sequence set forth in SEQ ID NO: 35 is a nucleic acid sequence set forth in SEQ ID NO: 41.

4. The nucleic acid aptamer of claim 1, wherein the nucleic acid aptamer comprises any one nucleic acid sequence selected from the group consisting of nucleic acid sequences set forth in SEQ ID NOs: 2 to 13.

5. The nucleic acid aptamer of claim 1, wherein the nucleic acid aptamer is a nucleic acid sequence set forth in SEQ ID NO: 2 (SQ2).

6. The nucleic acid aptamer of claim 1, wherein the nucleic acid aptamer is a nucleic acid sequence set forth in SEQ ID NO: 4 (SQ4).

7. The nucleic acid aptamer of claim 1, wherein the nucleic acid aptamer is a nucleic acid sequence set forth in SEQ ID NO: 36.

8. The nucleic acid aptamer of claim 1, wherein the nucleic acid aptamer is a nucleic acid sequence set forth in SEQ ID NO: 38.

9. The nucleic acid aptamer of claim 1, wherein the nucleic acid aptamer is a nucleic acid sequence set forth in SEQ ID NO: 39.

10. The nucleic acid aptamer of claim 1, wherein the nucleic acid aptamer is a nucleic acid sequence set forth in SEQ ID NO: 40.

11. The nucleic acid aptamer of claim 1, wherein the nucleic acid aptamer comprises a chemical modification.

12. The nucleic acid aptamer of claim 11, wherein the chemical modification is one in which the hydroxyl group at the 2' position of the ribose of at least one nucleotide included in the nucleic acid aptamer was replaced by any one of a hydrogen atom, a fluorine atom, an —O-alkyl group, an —O-acyl group and an amino group.

13. A method of detecting pancreatic cancer using the nucleic acid aptamer of claim 1 or a nucleic acid aptamer comprising a chemical modification thereof.

14. The method of claim 13, wherein the method comprising bringing the nucleic acid aptamer into contact with a sample selected from among pancreatic tissues, pancreatic cells, blood, serum, plasma, saliva, phlegm and urine.

15. A composition for diagnosing pancreatic cancer, which contains the nucleic acid aptamer of claim 1 or a nucleic acid aptamer comprising a chemical modification thereof.

16. A sensor for diagnosing pancreatic cancer, having the nucleic acid aptamer of claim 1 or a nucleic acid aptamer comprising a chemical modification thereof.

17. A method of detecting pancreatic cancer using the sensor of claim 16.

18. A kit for diagnosing pancreatic cancer, which contains the nucleic acid aptamer of claim 1 or a nucleic acid aptamer comprising a chemical modification thereof.

19. A method of detecting pancreatic cancer using the kit of claim 18.

20. A composition for treating pancreatic cancer, which contains the nucleic acid aptamer of claim 1 or a nucleic acid aptamer comprising a chemical modification thereof.

21. A pancreatic cancer-specific drug delivery composition containing the nucleic acid aptamer of claim 1 or a nucleic acid aptamer comprising a chemical modification thereof.

22. A method of detecting a pancreatic cancer cell-specific surface biomarker using the nucleic acid aptamer of claim 1 or a nucleic acid aptamer comprising a chemical modification thereof

* * * * *